US009980789B2

(12) United States Patent
Courtin et al.

(10) Patent No.: US 9,980,789 B2
(45) Date of Patent: May 29, 2018

(54) SYSTEM AND METHODS FOR ALIGNMENT OF A LASER BEAM

(71) Applicant: Convergent Dental, Inc., Natick, MA (US)

(72) Inventors: Christopher B. Courtin, Cambridge, MA (US); William H. Groves, Jr., Arlington, MA (US)

(73) Assignee: Convergent Dental, Inc., Needham, MA (US)

(*) Notice: Subject to any disclaimer, the term of this patent is extended or adjusted under 35 U.S.C. 154(b) by 362 days.

(21) Appl. No.: 14/959,764

(22) Filed: Dec. 4, 2015

(65) Prior Publication Data
US 2016/0157958 A1 Jun. 9, 2016

Related U.S. Application Data

(60) Provisional application No. 62/088,255, filed on Dec. 5, 2014.

(51) Int. Cl.
*G01B 11/00* (2006.01)
*A61C 1/00* (2006.01)
(Continued)

(52) U.S. Cl.
CPC .......... *A61C 1/0046* (2013.01); *A61B 18/201* (2013.01); *A61C 1/0015* (2013.01);
(Continued)

(58) Field of Classification Search
CPC ...... A61C 1/0046; A61C 1/085; G02B 7/005; G02B 26/0816; A61B 2018/00642; A61B 2018/202; H01S 3/0071
See application file for complete search history.

(56) References Cited

U.S. PATENT DOCUMENTS 3,551,057 A  12/1970 Hamilton et al.
3,876,309 A   4/1975 Zicaro et al.
(Continued)

FOREIGN PATENT DOCUMENTS

EP  0320573 A1   6/1989
EP  0345469 A1  12/1989
(Continued)

OTHER PUBLICATIONS

International Search Report for PCT/US2015/064084, dated Jun. 8, 2016.

*Primary Examiner* — Kara E Geisel
*Assistant Examiner* — Maurice Smith
(74) *Attorney, Agent, or Firm* — Goodwin Procter LLP

(57) ABSTRACT

A dental laser treatment system includes a treatment laser beam and a pilot (e.g., aiming/marking) laser beam sharing a collinear beam path, where the beam path is guided by a guidance system through a handpiece/main chamber assembly having a beam exit. A laser beam presence detector is removably affixed to or within the handpiece/main chamber assembly. The laser beam presence detector provides feedback to a computer which can control actuation of the treatment laser beam and the pilot laser beam, and the beam guidance system. The computer performs a search for determining the center location of the beam exit based on the feedback and controls the beam guidance system to guide the beam path approximately to the center of the beam exit, thereby providing automatic alignment of the laser beam with the beam exit or an optional hollow waveguide.

21 Claims, 15 Drawing Sheets

(51) Int. Cl.
  *A61C 3/02* (2006.01)
  *G02B 7/00* (2006.01)
  *G02B 26/08* (2006.01)
  *H01S 3/00* (2006.01)
  *A61B 18/20* (2006.01)
  *A61C 1/08* (2006.01)
  *A61B 18/00* (2006.01)

(52) U.S. Cl.
  CPC ............... *A61C 3/02* (2013.01); *G02B 7/005* (2013.01); *G02B 26/0816* (2013.01); *H01S 3/0014* (2013.01); *H01S 3/0071* (2013.01); *A61B 2018/00642* (2013.01); *A61B 2018/2025* (2013.01); *A61C 1/085* (2013.01)

(56) References Cited

U.S. PATENT DOCUMENTS

| | | |
|---|---|---|
| 3,915,574 A | 10/1975 | Hernqvist |
| 4,243,888 A | 1/1981 | Gruhn et al. |
| 4,294,544 A | 10/1981 | Altschuler et al. |
| 4,319,839 A | 3/1982 | Durran |
| 4,329,659 A * | 5/1982 | Chen .................... G02B 6/4202 372/38.01 |
| 4,539,462 A | 9/1985 | Plankenhorn |
| 4,626,649 A | 12/1986 | Dupeyrat et al. |
| 4,756,617 A | 7/1988 | Cain et al. |
| 4,772,122 A | 9/1988 | Kasner |
| 4,935,635 A | 6/1990 | O'Harra |
| 4,941,082 A | 7/1990 | Pailthorp et al. |
| 5,011,282 A | 4/1991 | Ream et al. |
| 5,033,061 A | 7/1991 | Hobart et al. |
| 5,049,147 A | 9/1991 | Danon |
| 5,103,082 A | 4/1992 | Fonneland et al. |
| 5,350,375 A | 9/1994 | Deckelbaum et al. |
| 5,536,916 A | 7/1996 | Kohari et al. |
| 5,598,269 A | 1/1997 | Kitaevich et al. |
| 5,616,908 A | 4/1997 | Wilz et al. |
| 5,778,043 A | 7/1998 | Cosman |
| 5,810,841 A | 9/1998 | McNeirney et al. |
| 5,970,433 A * | 10/1999 | Oka .................... G01S 7/4811 250/559.13 |
| 6,014,206 A | 1/2000 | Basting et al. |
| 6,253,160 B1 | 6/2001 | Hanseder |
| 6,288,381 B1 | 9/2001 | Messina |
| 6,339,470 B1 | 1/2002 | Papademetriou et al. |
| 6,501,061 B1 | 12/2002 | Kitai et al. |
| 6,606,339 B1 | 8/2003 | Greninger |
| 6,666,855 B2 | 12/2003 | Somani et al. |
| 6,694,169 B2 | 2/2004 | Kennedy, II et al. |
| 6,726,680 B1 | 4/2004 | Knopp et al. |
| 6,737,664 B2 | 5/2004 | Shaffer et al. |
| 6,750,953 B1 | 6/2004 | Douglas |
| 6,816,535 B2 | 11/2004 | Ho et al. |
| 7,274,718 B2 | 9/2007 | Tan et al. |
| 7,352,944 B2 | 4/2008 | Yang |
| 7,447,565 B2 | 11/2008 | Cerwin |
| 7,452,500 B2 | 11/2008 | Uckelmann |
| 7,594,752 B2 | 9/2009 | Rockseisen |
| 7,878,657 B2 | 2/2011 | Hajjar |
| 8,288,679 B2 | 10/2012 | Unrath |
| 8,379,204 B1 | 2/2013 | Cordingley et al. |
| 8,451,195 B2 | 5/2013 | Hajjar et al. |
| 8,537,203 B2 | 9/2013 | Seibel et al. |
| 8,675,141 B2 | 3/2014 | Miller |
| 8,766,213 B2 | 7/2014 | Straw et al. |
| 8,779,326 B2 | 7/2014 | Rumsby |
| 2003/0206614 A1 | 11/2003 | Kendrick et al. |
| 2008/0043237 A1 | 2/2008 | Grimm et al. |
| 2008/0255411 A1* | 10/2008 | Kobayashi ......... A61B 1/00059 600/104 |
| 2009/0067189 A1* | 3/2009 | Boutoussov ........... A61B 18/20 362/553 |
| 2009/0131922 A1 | 5/2009 | Dewey et al. |
| 2010/0060900 A1 | 3/2010 | Quadling et al. |
| 2012/0206583 A1* | 8/2012 | Hoshi .................... A61B 1/042 348/76 |
| 2012/0232542 A1 | 9/2012 | Kasenbacher |
| 2014/0080087 A1 | 3/2014 | Monty |
| 2014/0272775 A1 | 9/2014 | Monty |

FOREIGN PATENT DOCUMENTS

| | | |
|---|---|---|
| EP | 1088523 A1 | 4/2001 |
| JP | 60159714 | 8/1985 |
| JP | 61198158 | 9/1986 |
| JP | 08103881 | 4/1996 |
| JP | 09099386 | 4/1997 |
| JP | 3625916 B2 | 3/2005 |
| JP | 05256628 B2 | 8/2013 |
| WO | WO-1998024514 A1 | 6/1998 |
| WO | WO-00/16152 A1 | 3/2000 |
| WO | WO-00/19919 A1 | 4/2000 |
| WO | WO-00/53261 A1 | 9/2000 |
| WO | WO-02/13905 A1 | 2/2002 |
| WO | WO-2007027562 A1 | 3/2007 |
| WO | WO-2010089693 A1 | 8/2010 |
| WO | WO-2010118146 A1 | 10/2010 |
| WO | WO-2014049132 A1 | 4/2014 |

* cited by examiner

SYSTEM AND METHODS FOR ALIGNMENT OF A LASER BEAM

CROSS-REFERENCE TO RELATED APPLICATIONS

This application claims the benefit of priority to U.S. Provisional Patent Application No. 62/088,255, entitled "Systems and Methods for Alignment of a Laser Beam," filed Dec. 5, 2014, the disclosure of which is incorporated herein by reference in its entirety.

FIELD OF THE INVENTION

The present disclosure relates generally to a laser-based treatment system and, in particular, to systems and methods for aligning the laser beam using a feedback-controlled beam guidance system.

BACKGROUND

Lasers are increasing being shown to be useful in a multitude of hard and soft tissue dental procedures, including: removing decay; cutting, drilling or shaping hard tissue; and removing or cutting soft tissue. A tooth has three layers: the outermost layer is the enamel which is the hardest and generally forms a protective layer for the rest of the tooth, the middle and bulk of the tooth includes dentin, and the innermost layer includes pulp. The enamel and dentin are similar in composition and include roughly 85% mineral, generally carbonated hydroxyapatite, while the pulp contains vessels and nerves. Laser radiations at wavelengths in the 9.3-9.6 micrometer range are well absorbed by the hydroxyapatite that forms a significant portion of tooth and bone, making such lasers efficient in the removal of hard tissue.

Lasers have also been found to be useful in the removal of dental material without needing local anesthetic that is typically required when a similar procedure is performed using a drill. Further, lasers do not make the noises and vibrations that are associated with dental drills. At least for these reasons, it is the hope of many in the dental industry that lasers may replace the drill and may eliminate or at least lessen the anxiety and fear from dental treatment.

A dental treatment laser having a wavelength in the 9.3-9.6 micrometer range is not visible to the human eye. Therefore, in addition to the treatment laser beam, a dental laser system may employ a marking/aiming laser beam in the visible spectrum. Such lasers may have a wavelength of about 532 nanometers (which is a green laser) or 650 nanometers (which is a red laser). If the marking laser beam and the treatment laser beam are collinear along a beam path, it is likely that the treatment laser beam will act upon substantially the same area where the marking laser beam impinges.

In many dental laser systems, the laser is housed in a console and is transmitted to a handpiece/main chamber assembly through an articulated or flexible arm, using optical devices such as mirrors, lenses, and/or fiber optic cables. The arm generally attaches to a main chamber to which a handpiece attaches, as well. The handpiece can be made detachable, e.g., for cleaning, servicing, etc. Differently configured handpieces, that are detachable, may be used for different dental procedures. At the end of the arm or within the main chamber, a beam guidance system may be located, that can be used to guide the laser beam towards a selected treatment area. The handpiece beam exit from which the laser beam exits is typically small for improved ergonomics and easier manipulation, e.g., within a person's mouth during laser-based dental treatment. It is usually desirable that the laser beam pass through approximately the center of the beam exit, so that an operator can target the handpiece toward a center of the area to be treated. The beam guidance system can then automatically move the laser beam according to certain shape, size, and scan parameters, such that at least a portion of the area to be treated around the targeted center is irradiated for fast, efficient, and effective treatment.

The beam guidance system may control the movement of the treatment laser beam to treat a portion of the tissue to be treated, where the portion has a particular preset shape. Alternatively, or in addition, an operator may specify a perimeter of the treatment area. A computer (any processor or processing unit, at least a part of which includes software) containing coordinates for a series of preset shapes and/or the user-specified perimeter may control the movement of the beam guidance system. To this end, a beam guidance system generally includes a pair of computer-controlled galvanometers. U.S. Patent Application Publication No. 2013/0059264 describes such a beam guidance system, and is incorporated herein by reference in its entirety.

There are numerous potential sources of position alignment error in the guidance of laser beams, particularly in a dental laser system. Often the alignment of the laser beam undergoes variations over time. These variations can result from: system vibrations, the system getting bumped, misalignment of different interchangeable handpieces, misalignment of the articulated arm, optical misalignment, geometric stacking errors, mechanical and/or electrical drift, and/or thermal deformations. The effects of beam alignment variation may combine over time and can result in a significant alignment degradation, that can prevent a proper, effective, and/or efficient use of the laser-based treatment system. Variability of laser beam alignment may adversely affect reliability of many laser-based treatment devices and especially of those devices that are equipped with articulated arm type beam delivery systems. Alignment of the laser beam in laser-based treatment devices is often a time consuming process that requires trained personnel and needs to be repeated on a regular basis.

SUMMARY

In various embodiments, an efficient, accurate, and user-friendly system for automatic alignment of a dental laser beam proximate the treatment area can accurately guide a laser beam through a handpiece/main chamber assembly, through a beam exit of the handpiece towards an area/region of tissue to be treated. This is achieved, at least in part, using a laser beam presence detector providing feedback to a computer (any processor or processing unit, at least a part of which may include software), that controls actuation and guidance of the laser beam. In some embodiments, the laser beam path is aligned with the center of the beam exit.

In general, in one aspect, embodiments of the disclosure feature a beam-alignment system for aligning a laser beam of a laser-based treatment apparatus. The system may include a housing forming an inlet to a beam exit of a handpiece of the laser-based treatment apparatus and a sensor disposed in the housing. The sensor may be aligned with the inlet and adapted to provide a first signal indicating detector of laser energy above a specified threshold level and a second signal indicating absence of laser energy above the threshold level (or in some cases, absence of laser energy).

In various embodiments, the housing is detachable to the beam exit via at least one of: a friction-based coupling, a threaded coupling, a magnetic coupling, and a mechanical coupling. The sensor may be one or more of a photoresistor, a photodiode, a phototransistor, a thermoelectric device, and/or a far-IR optical sensor. The system can include a diffuser disposed over the sensor, which may include a translucent material. The system can include an amplifier for amplifying an output signal of the sensor. In some instances, the system also features circuitry that (i) compares a sensor signal obtained from the sensor with a reference signal and (ii) produces the first signal if the sensor signal is greater than the reference signal and otherwise produces the second signal. In some instances, the system includes a processor programmed to (i) direct a beam guidance system to adjust a laser beam path and (ii) determine a center of the beam exit using the first and second signals.

In general, in another aspect, embodiments of the disclosure feature a laser-based treatment system including a handpiece having a beam exit and a sensor assembly. The sensor assembly may have a central aperture aligned with the beam exit and may be at least partially attached to an inner surface of the handpiece. The sensor assembly can be adapted to provide a first signal indicating detection of laser energy by the sensor assembly above a specified threshold level and a second signal indicating absence of laser energy above the specified threshold level.

In various embodiments, at least a portion of the inner surface of the handpiece is reflective at a wavelength of the laser. The sensor can include one or more of a photoresistor, a photodiode, a phototransistor, a thermoelectric device, and/or a far-IR optical sensor. The handpiece can also include a turning mirror. In some instances, the turning mirror is disposed downstream of the sensor along a first portion of a laser-beam path and upstream from the beam exit along a second portion of the laser-beam path and the beam exit and the aperture of the sensor assembly are aligned via the first and second portions. A translucent material may be disposed over the sensor assembly. The system can include an amplifier for amplifying an output signal of the sensor assembly. In some instances, the system also features circuitry that (i) compares a sensor signal obtained from the sensor with a reference signal and (ii) produces the first signal if the sensor signal is greater than the reference signal and otherwise produces the second signal. In some instances, the system includes a processor programmed to (i) direct a beam guidance system to adjust a laser beam path and (ii) determine a center of the beam exit using the first and second signals. In certain implementations, the sensor assembly includes an annular reflector (e.g., a diffusor) attached to the inner surface of the handpiece and having the central aperture and a sensor separated from and facing the reflector ring and adapted to produce the first and second signals.

In general, in another aspect, embodiments of the disclosure feature a laser-based treatment system that includes a beam guidance system, directing a laser beam along a beam path and a handpiece having one or more of a beam exit for directing the laser beam towards a treatment area and/or a hollow waveguide. The system can also include a sensor assembly and a processor programmed to receive a plurality of signals from the sensory assembly and, in response, control an initial position of the beam guidance system to adjust the beam path through a center of one of (i) the beam exit and (ii) an inlet of the hollow waveguide.

In various embodiments, the beam guidance system includes a pair of galvanometer controlled mirrors. At least a portion of the sensor assembly can be housed within the handpiece. The sensor assembly can be located in a detachable housing. In some cases, at least one of (i) an electrical communication link between the sensor assembly and the processor and (ii) an electrical communication link between the processor and the beam guidance system, is a wireless communication link.

In general, in another aspect, embodiments of the disclosure feature a method of aligning a laser beam. The method may include the step of controlling, by a processor, a beam guidance system to direct a laser beam along a first beam path so that the laser beam is detected by a sensor and controlling, by the processor, the beam guidance system to adjust a path of the laser beam up to a second beam path so that the sensor detects an absence of the laser beam. The method can include recording, by the processor, a first set of co-ordinates associated with the beam guidance system and corresponding to the second beam path. The method may include controlling, by a processor, a beam guidance system to direct a laser beam along one of the first beam path and a third beam path, so that the laser beam is detected by an sensor and controlling, by the processor, the beam guidance system to adjust a path of the laser beam up to a fourth beam path so that the sensor detects an absence of the laser beam. The method can include recording, by the processor, a second set of co-ordinates associated with the beam guidance system and corresponding to the fourth beam path. The method may include computing, by the processor, a set of co-ordinates associated with a beam exit.

In various embodiments, the method can also include adjusting, by the processor, an initial position of the beam guidance system using the set of co-ordinates associated with the beam exit. The laser beam may be one or more of a treatment laser beam and/or a marking laser beam. In some cases, the method also includes directing, by the beam guidance system, the laser beam according to a specified pattern, shape, and size. In various instances, the step of adjusting the initial position of the beam guidance system is performed (i) prior to the directing step and (ii) during two iterations of the directing step.

In general, in another aspect, embodiments of the disclosure feature another method of aligning a laser beam. The method may include the steps of: (a) selecting a first axis and a step size and (b) adjusting a first rotatable mirror of a beam guidance system such that a laser beam directed by the beam guidance system is not detected by a sensor and recording a co-ordinate of the first mirror along the first axis. The method can also include (c) adjusting the first rotatable mirror along the first axis in a first direction by the step size and recording a co-ordinate of the first mirror along the first axis. If the laser beam is not detected, the method can include (d) increasing the step size and repeating step (c). If the laser beam is detected, then the method can include (e): (A) decreasing the step size and readjusting the first rotatable mirror along the first axis in a second direction that is opposite of the first direction by the decreased step size. If the laser beam is detected, the method can include (B) computing an average of the co-ordinates recorded in steps (b) and (c), the average being associated with the first rotatable mirror. If the laser beam is not detected, the method can include (C) replacing the co-ordinate recorded in step (b) corresponding to the readjusted position of the first rotatable mirror along the first axis; and (D) decreasing the step size and readjusting the first rotatable mirror along the first axis in the first direction by the decreased step size. If the laser beam is not detected, the method can include (E) computing an average of the co-ordinates recorded in steps (C) and (c), the average being associated with the first rotatable mirror. If the laser beam is detected, the method can include (F) replacing the co-ordinate recorded in step (c) corresponding to the readjusted position of the first rotatable mirror along the first axis.

In various embodiments, the method includes repeating steps (e)(A) through (e)(F). The method can also include selecting a second axis orthogonal to the first axis and repeating steps (b) through (e) corresponding to the second axis and a second rotatable mirror, the average computed in any of steps (e)(B) and (e)(E) being associated with the second rotatable mirror.

In general, in another aspect, embodiments of the disclosure feature a laser-based treatment system facilitating automatic alignment of a laser beam. The system can include a beam guidance system adapted to direct a laser beam through an aperture. The system can feature a sensor adapted to provide a feedback signal in response to the laser beam passing through the aperture. The system may have a processor adapted to (i) determine a center of the aperture based on the feedback signal and (ii) adjust the beam guidance system for directing the laser beam through the aperture center.

In various embodiments, the beam guidance system includes a pair of galvanometer-controlled mirrors, each galvanometer of the pair being controlled by the processor. In some cases, the system can include a handpiece in which the aperture is a beam exit of the handpiece. In other cases, the handpiece may have a hollow waveguide in which the aperture is an inlet of the hollow waveguide. In other cases, the sensor is an annular sensor disposed in the handpiece and the aperture includes an opening in the annular sensor. In certain instances, the system includes a handpiece and an annular reflector disposed within the handpiece, in which the aperture is an opening in the annular reflector. In such instances, the sensor can be oriented to face the annular reflector. The system may also include a diffusor having a translucent material disposed over the annular reflector (or in some cases, the sensor). The aperture can be located upstream along a beam path from a beam exit of the handpiece. In some cases, the sensor is adapted to provide a first feedback signal indicating detection of laser energy by the sensor above a specified threshold level and a second feedback signal indicating absence of laser energy above the threshold level (e.g., absence of laser energy). The sensor may include one or more of a photoresistor, a photodiode, a phototransistor, a thermoelectric device, and/or a far-IR optical sensor. The system can include an amplifier for amplifying an output signal of the sensor. In some instances, the system also include circuitry that (i) compares a sensor signal obtained from the sensor with a reference signal and (ii) produces a first feedback signal if the sensor signal is greater than the reference signal and otherwise produces a second feedback signal.

In general, in another aspect, embodiments of the disclosure feature a dental laser treatment system that includes at least one laser beam having a beam path, a beam guidance system located within the beam path, a beam exit located after the beam guidance system and within the beam path, and a laser beam presence detector in proximity to the beam exit. The beam exit may have a center location and the laser beam presence detector may provide feedback in response to the beam exit being with the beam path. The beam guidance system may respond to the feedback, such that the beam path is guided to the center location of the beam exit.

In various embodiments, the laser beam is a pilot laser beam having a visible light wavelength (e.g., approximately 532 nanometers). The system may also include a treatment laser beam having an infra-red wavelength (e.g., approximately 9.3-9.6 micrometers). In some instances, the treatment laser beam and the pilot laser beam are collinear. The laser beam presence detector may be configured to detect visible light and/or infra-red light. The system may further include a handpiece assembly disposed downstream of the beam guidance system, in which the beam exit is a portion of the handpiece assembly. In some instances, the laser beam presence detector may be removably affixed to the handpiece assembly in proximity to the beam exit. For example, the laser beam presence detector may be disposed inside the handpiece assembly and upstream of the beam exit. The handpiece assembly can be interchangeable. The system may also include a turning mirror which is disposed inside the handpiece assembly in proximity to the beam exit and within the beam path. In some cases, the turning mirror is disposed upstream of the laser beam presence detector within the beam path. In other cases, the turning mirror is disposed between the laser beam presence detector and the beam exit within the beam path.

In various embodiments, the beam guidance system features a beam guidance element that may include galvanometers (e.g., two galvanometers), mirrors, lenses, electro-optic scanners, in-line beam steerers, prisms, dual-wedge scanners, polarization gratings, and/or piezo transducer based beam steering components. In certain instances, the system further includes a galvanometer controller configured to control the movement of the beam guidance system and a computer that receives feedback from the beam presence detector. The computer may be in electronic communication with the galvanometer(s) through a control signal path. In some cases, the beam guidance system is disposed within the handpiece assembly. The laser beam presence detector may also include at least one optical or other sensor and a sensor housing enclosing the sensor. The sensor may provide feedback via a device for performing signal communication (e.g., an electrically conductive device, a wireless signaling device, etc.), and the sensor housing may enable attachment of the laser beam presence detector to the handpiece assembly. In some cases, the sensor can be one or more of photoresistors, photodiodes, phototransistors, Peltier devices, and/or far-IR optical sensors. The sensor housing may be opaque. In certain implementations, the system also includes an optical integration element covering at least a portion of the optical sensor.

In general, in another aspect, embodiments of this disclosure feature a dental laser treatment system that includes a treatment laser beam operating in the infra-red spectrum and a pilot laser beam operating in the visible spectrum, in which the treatment laser beam and the pilot laser beam are collinear and form a beam path. The system may include a pair of galvanometers disposed within the beam path and a handpiece assembly having a beam entry and a beam exit. The beam entry may be disposed after the galvanometers within the beam path and the beam exit may be disposed after the beam entry within the beam path. The beam exit has a center location. The system may also include a laser beam presence detector removably affixed to the handpiece assembly in proximity to the beam exit and which provides a feedback to a computer. The computer may control actuation of the treatment laser beam and the pilot laser beam, as well as movement of the galvanometers. The computer may have a search algorithm that determines the center location of the beam exit based on the feedback. The computer may control movement of the galvanometers to guide the beam path to the center location to provide automatic alignment.

In various embodiments, the laser beam presence detector is configured to detect visible light. The laser beam presence detector may be disposed inside the handpiece assembly and upstream of or before the beam exit. In some implementations, the system may also include a galvanometer controller configured to control the movement of the galvanometers and the computer may be in electronic communication with the galvanometer controller through a control signal path. The handpiece assembly may be interchangeable. In some implementations, the system also includes a turning mirror disposed inside the handpiece assembly in proximity to the beam exit and within the beam path. In some implementations, the turning mirror is disposed before the laser beam presence detector within the beam path. In other implementations, the turning mirror is disposed between the laser beam presence detector and the beam exit within the beam path.

In various embodiments, the laser beam presence detector also includes at least one optical or other sensor, a device for performing signal communication between the optical sensor and the computer (e.g., an electrically conductive device, a wireless signaling device, etc.), and a sensor housing enclosing the optical sensor. The sensor housing may enable attachment of the laser presence detector to the handpiece assembly. The sensor housing may be opaque. In some instances, the system also features an optical integration element that covers at least a portion of the optical sensor.

In general, in another aspect, embodiments of the present disclosure feature a method of aligning a laser beam. The method may include the step of adjusting by a processor, using a feedback signal received from a sensor, a beam guidance system, to direct a laser beam such that the sensor produces a first signal indicating absence of a laser beam incident upon the sensor. The method may also include adjusting by a processor, using the feedback signal received from the sensor, the beam guidance system, to direct the laser beam such that the sensor produces a second signal indicating that the laser beam is incident upon the sensor. The method can include determining by the processor a perimeter of a beam exit based at least in part on the adjustments of the beam guidance system. In some instances, the method includes computing by the processor a center of the beam exit, at least in part, using the perimeter of the beam exit. The method can also include adjusting by the processor an initial position of the beam guidance system, such that the beam passes approximately through the center of the beam exit.

BRIEF DESCRIPTION OF THE FIGURES

Various aspects this disclosure will become more apparent in view of the attached drawings and accompanying detailed description. The embodiments depicted therein are provided by way of example, not by way of limitation, wherein like reference numerals generally refer to the same or similar elements. In different drawings, the same or similar elements may be referenced using different reference numerals. The drawings are not necessarily to scale, emphasis instead being placed upon illustrating various aspects of the invention. In the drawings.

DETAILED DESCRIPTION

In some dental laser treatment systems, a suitable wavelength range for the treatment laser beam is approximately in a range from 9.3-9.6 micrometers. In this infra-red range, the laser beam is not visible. The treatment laser beam may operate with sufficient power to cut, ablate, cauterize, and/or otherwise affect dental tissue. As such, it is beneficial for the operator (e.g., a dentist, surgeon, other medical personnel, etc.) to know, prior to and/or during treatment, the location of a spot on the treatment area where the treatment laser beam would impinge. To this end, a marking/aiming laser beam in the visible spectrum may be used. In various embodiments, the marking/aiming laser beam is low powered and may mark the treatment location. One example marking laser beam is green and has a wavelength of approximately 532 nanometers. If the treatment laser beam and the marking laser beam are collinear, the treatment laser beam would impinge upon the treatment surface substantially (e.g., with a true position tolerance of less than 0.1%, 0.5%, 1%, 2%, 5%, etc.) at the location where the marking/aiming laser beam impinged. In the discussion below, the term laser beam, though it represents both the marking and treatment laser beams, generally refers to the marking laser beam.

Figure 1:
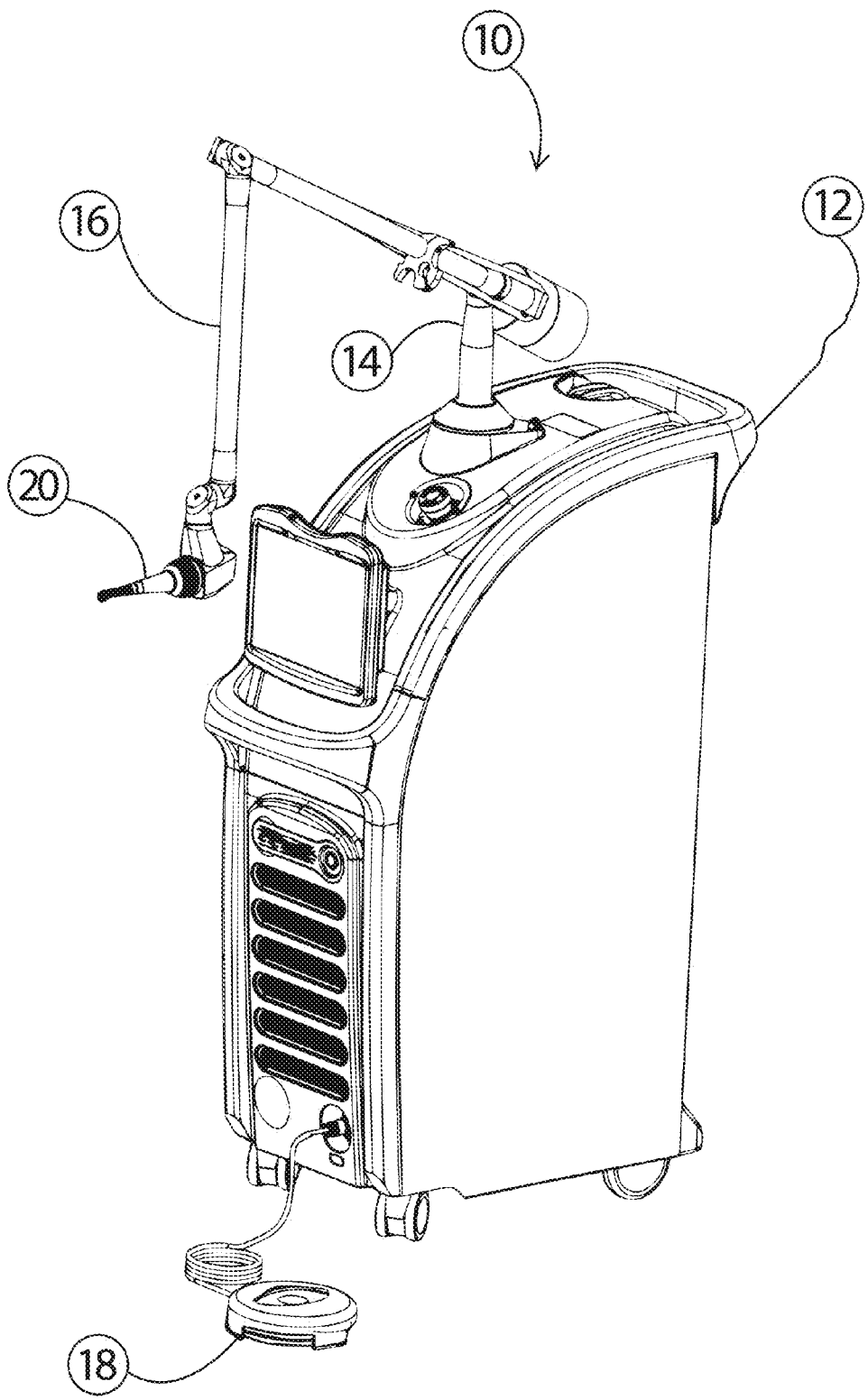
FIG. 1 is an isometric view of an exemplary dental laser system.

FIG. 1 shows an example dental laser system 10 containing at least one laser source 12 producing at least one laser beam. A launch 14 is connected between the main portion of the dental laser system 10 and an articulated arm 16. The launch 14 encloses and guides the laser beam into the articulated arm 16. The articulated arm 16 may include multiple articulated sections which serve to enclose and guide the laser beam into a handpiece/main chamber assembly 20. A laser beam transport system within the articulated arm may include one or more of mirrors, lenses, prisms, fiber optic cables, and/or other optical elements. The handpiece/main chamber assembly 20 is attached to the end of the articulated arm 16 and may be interchangeable by the user. At least one control 18 of the laser system 10 may be configured for use remotely from the main portion of the dental laser system 10.

Figure 2:
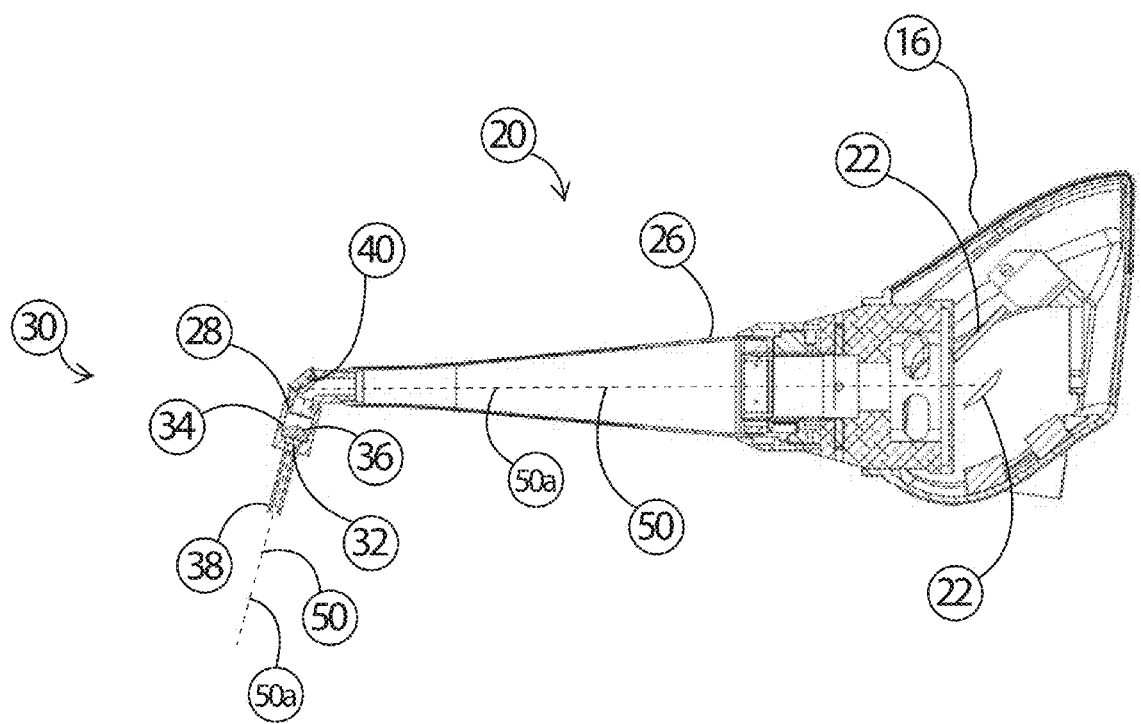
FIG. 2 is a cross-sectional view of a dental laser handpiece/main chamber assembly, a laser beam presence detector, and galvanometers, according to various embodiments.
Figure 3:
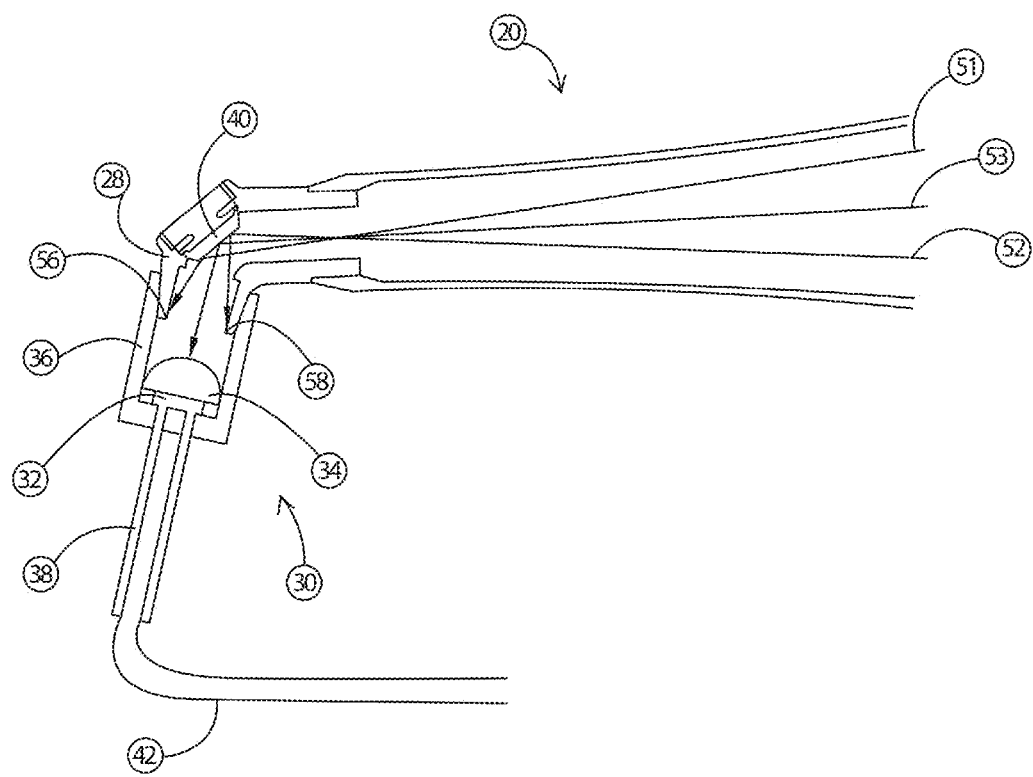
FIG. 3 is an enlarged cross-sectional view of a portion of a dental laser handpiece/main chamber assembly and a laser beam presence detector, according to various embodiments.

FIGS. 2 and 3 show an example handpiece/main chamber assembly 20 attached to the end of the articulated arm 16. The assembly 20 includes a pair of galvanometers 22 that can move attached mirrors to guide a laser beam to a certain specified location. As used herein, the term galvanometer generally refers to an assembly that includes the actuator portion of an electromagnetically steerable mirror and the rotatable mirror attached to the actuator, as well. Other beam guidance elements, including mirrors, lenses, electro-optic scanners, in-line beam steerers, prisms, dual-wedge scanners, polarization gratings, and piezo transducers, may be used additionally or in the alternative for beam steering. The handpiece/main chamber assembly 20 has a beam entry 26 proximate the end of the articulated arm 16 and the galvanometers 22. The handpiece/main chamber assembly 20 has a beam exit 28 at the end opposite the beam entry 26. The beam entry 26 and beam exit 28 may be in-line with a straight beam path therethrough or, as shown, a turning mirror 40 may be disposed therebetween, along the beam path 50 and in proximity to the beam exit 28. Thus, the beam may exit the handpiece/main chamber assembly 20 such that upstream and downstream beam-path portions 50a and 50b of the beam path 50 are at an angle relative to each other.

In some instances, a laser beam presence detector 30 is attached proximate the beam exit 28 portion of the handpiece/main chamber assembly 20. Typically, the turning mirror 40 is disposed upstream or before the laser beam presence detector 30 within the beam path 50. The laser beam presence detector 30 may include an optical or other sensor 32 located approximately in the center of the beam exit 28, a sensor housing 36 enclosing the optical sensor 32 and for attaching the laser beam presence detector 30 to the handpiece/main chamber assembly 20 in proximity to the beam exit 28, and an optical integration element 34 covering the optical sensor 32. The optical integration element 34 may diffuse the laser beam before it reaches the optical sensor 32. The optical sensor 32 may have a pair of optical sensor output leads 38, which can provide electrical output through a pair of sensor output wires 42 or any other suitable electrical conductors.

In various embodiments, the laser beam presence detector 30 is affixed in proximity to the beam exit 28 portion of the handpiece/main chamber assembly 20 in order to perform laser beam alignment and is typically removed after laser beam alignment, so that the dental laser treatment system 10 can be used to direct the treatment and/or marking laser beams to the tissue to be treated. The sensor 32 may include a photo- or thermo-sensitive detection element including, but not limited to, photoresistors, photodiodes, phototransistors, Peltier thermoelectric devices, and far-IR optical sensors. The laser beam presence detector 30 may be configured to detect the visible light of the marking/aiming laser beam and, additionally or in the alternative, may be configured to detect the infra-red light of the treatment laser beam. The sensor housing 36 is usually opaque to block ambient light and can be removably affixed to the handpiece/main chamber assembly 20 by friction, a threaded connection, a magnetic connection, a slight mechanical interference fit, etc. The optical integration element 34 may include translucent foam, or any other translucent material that can transmit and substantially evenly diffuse the incident laser light. In some embodiments, the optical integration element 34 may cover the entire surface of the optical sensor 32. In some embodiments, the optical integration element 34 may cover only a portion of the surface of the optical sensor 32.

With reference to FIG. 3, a laser beam propagating along a first beam path 51 used for system calibration is shown as reflecting off the turning mirror 40 and contacting a boundary of the beam exit 28 of the handpiece/main chamber assembly 20 at a location 56. The laser beam may then be reflected off the inner surface of the beam exit and at least some of the laser energy may be sensed by the optical sensor 32. By initially contacting the boundary 56, however, the laser beam propagating along the beam path 51 will not contact the optical sensor 32 with the intensity corresponding to direct impingement via beam path 53. Likewise, a laser beam propagating along a beam path 52 also reflects off the turning mirror 40 and contacts the beam exit boundary at a location 58, from where it may be reflected again and may not contact the optical sensor 32 with the intensity corresponding to direct impingement. In various cases, the laser beam may not be reflected off the inner surface by the beam exit 28 and, as such, may not be sensed at all by the optical sensor 32. A laser beam propagating along beam path 53 reflects off the turning mirror 40 and directly impinges upon the optical sensor 32.

Figure 4:
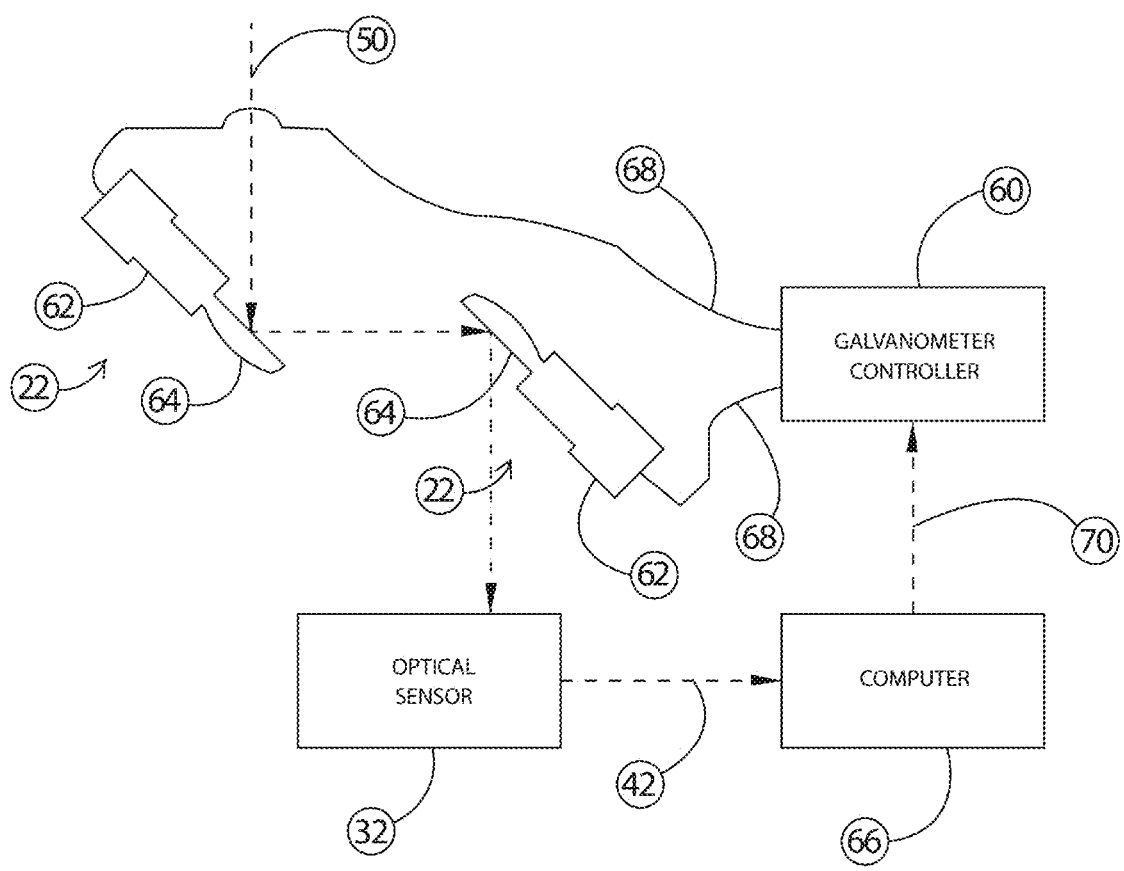
FIG. 4 is a block diagram of an automatic alignment system, according to various embodiments.

With reference to FIG. 4, galvanometer mirrors 64 of the galvanometers 22 guide a laser beam along the path 50, such that it may or may not impinge directly upon the optical sensor 32. A sensor signal generated by the sensor 32 may be transmitted to a computer 66 via the sensor output wires 42 connected to the sensor leads 38. In some embodiments, circuitry such as a signal conditioner/filter, amplifier, etc., is associated with the optical sensor 32. The computer 66 may include a processor or a processing unit, at least a part of which includes software, and/or circuitry such as a chip, a field programmable gate array, etc. In some embodiments, the computer 66 implements a search procedure described below.

The computer 66 can control the beam guidance system through a control signal path 70 to a galvanometer controller 60 in electrical communication with the galvanometer actuators 62 of the galvanometers 22 via galvanometer control signal paths 68. The galvanometer actuators 62 can rotate the galvanometer mirrors 64, thus changing the beam path 50 through the handpiece/main chamber assembly 20 to selected or programmed locations of the treatment area/region through the beam exit 28. The computer 66 can also control laser-beam actuation and can synchronize galvanometer 22 movements and laser beam pulses. A feedback system may control automatically the alignment of the galvanometers 22 and thus a position of the beam path 50 relative to the beam exit 28, as described below.

In some embodiments, the laser beam is actuated by the computer 66. The computer 66 also commands the galvanometer controller 60 to sweep the galvanometer mirrors 64 through a predetermined angular range of movement. Within a portion of this range of galvanometer movement, the beam path 50 impinges directly on the optical sensor 32. As such, the optical sensor 32 detects the laser beam impinging thereupon and produces an electrical signal representing that the laser beam impinged upon the optical sensor 32. This signal can be transmitted through the sensor output leads 38 and the sensor output wires 42 to the computer 66.

Within other portions of the range of galvanometer movement, the beam path 50 is directed to the edges of the handpiece/main chamber assembly 20 at the beam exit 28. As such, the laser beam is blocked by or reflected off of the perimeter of the beam exit and does not impinge directly upon the sensor 32. In these cases, where the laser beam is reflected by the beam exit 28 and impinges upon the optical sensor 32, but not at the intensity required for detection, the optical sensor 32 may transmit an electrical signal indicating that a laser beam was detected at a low level (or not at all) by the optical sensor 32 to the computer 66. In some embodiments, the optical sensor 32 and the associated circuitry can generate a signal indicative of the strength (e.g., fluence) of the laser beam detected by the sensor 32.

In some embodiments, the optical sensor 32 is generally supplied with sensor output leads 38. The sensor output wires 42 are fastened to the sensor output leads 38 during assembly of the laser beam presence detector 30. Alternatively, the sensor output wires 42 may be attached directly to the optical sensor 32, without using the leads 38. The electrical signal indicating that the laser beam was not detected can be a null or zero signal (e.g., a 0 V or a 0 A signal). The electrical signal can, however, be any other type of low level signal, as long as the computer 66 can determine by interpreting the signal whether the beam path 50 directly impinges the optical sensor 32 or not.

Referring again to FIG. 3, the beam paths 51, 52 illustrate how a laser beam propagating along either of these paths may be blocked by the edges of the handpiece/main chamber assembly 20 at the beam exit boundaries 56, 58, respectively. The optical integration element 34 can diffuse and thus average any laser radiation that is incident upon the surface of the optical sensor 32. The detection of laser energy may be performed by the optical sensor 32 using or without using the optical integration element 34. In some embodiments, the optical sensor 32 includes an analog sensor. The computer 66 may interpret the signals received from the optical sensor 32 as discrete binary signals either indicating that laser radiation is incident upon the optical sensor 32, or that no laser radiation or laser radiation with energy below a variable or specified threshold is incident upon the optical sensor 32. In this mode of use, the detection and processing of incident laser radiation is generally employed to perform edge detection. The electrical signal indicating whether a laser beam is sensed or is not sensed can provide feedback to the computer 66 via the feedback system described above with reference to FIG. 4. The computer 66 can adjust the galvanometer controller 60 and, in turn, the galvanometers 62, as described below.

In some embodiments, the computer 66 includes a perimeter search procedure that may record the galvanometer position coordinates in general and, specifically, when the optical sensor 32 output signal indicates a transition from not sensing an incident laser beam/radiation to sensing an incident laser beam/radiation. During the perimeter search, the computer 66 may also record the galvanometer position coordinates when the optical sensor 32 output signal indicates a transition from sensing an incident laser beam/radiation to not sensing an incident laser beam/radiation. Each of these sets of position coordinates can define a point on the edge or the perimeter of the beam exit 28. If the beam exit is circular, the position coordinates for the center of the beam exit 28 can be calculated by determining the position coordinates for three or more points on the perimeter of the beam exit 28.

Once the position coordinates for the center of the beam exit 28 are calculated, the computer 66 may transmit a computer control signal via the computer control signal path 70 to the galvanometer controller 60, which in turn may transmit galvanometer control signals via the galvanometer control signal paths 68 to the galvanometer actuators 62. The galvanometer mirrors 64 may then be moved such that the beam path 50 may be adjusted to pass through the center of the beam exit 28. In various embodiments, such an adjustment can be achieved within a tolerance of 0.01%, 0.05%, 0.1%, 1%, 2%, 5%, 10%, 20%, etc., of a diameter of the beam exit 28 (or another suitable cross-sectional dimension thereof, if the beam exit 28 is not circular). If the beam exit 28 is not circular, more than three edge locations on the perimeter thereof, e.g., one or more edge locations on one or more edges of the beam exit 28, can be determined using the perimeter search procedure described above. Thus, the computer 66, provided with a position feedback input from the optical sensor 32, can control the movement of the beam guidance system so that in an initial position thereof, the laser beam passes approximately through the center location of the beam exit 28 and impinges upon a selected spot on the tissue region to be treated. Thereafter, the galvanometer controller 60 may move the galvanometers 62 so as to scan a region of a specified size and shape around the selected spot so as to automatically, uniformly, and efficiently treat that region.

In various embodiments, different search algorithms may be used to perform the edge detection described above. In general, the feedback-based method can be used with the search procedure to determine the center of the beam exit 28, and thus can enable automatic alignment of the galvanometer mirrors 64 during production/manufacturing, field service, or by the user, e.g., prior to performing a selected treatment procedure. Such an automatic alignment calibration can correct for a range of positioning errors generally resulting from circumstances including, but not limited to, system vibrations during operation, accidental bumping of the treatment system, misalignment of different interchangeable handpiece/main chamber assemblies 20, misalignment of the articulated arm 14, other optical misalignments, mechanical and/or electrical drift, thermal deformation of one or more system components, etc.

In some embodiments, the optical sensor 32 used for detecting the laser beam is placed inside the handpiece/main chamber assembly 20 such that the sensor 32, i.e., the beam presence detector 30, is located between the turning mirror 40 and the beam exit 28. Additionally or in the alternative, in some embodiments, the turning mirror 40 is disposed between the optical sensor 32/beam presence detector 30 and the beam exit 28. The galvanometers 22 may be moved and the initial position thereof may be adjusted as described above. In these embodiments, the laser beam presence detector 30 forms a central opening permitting passage of the laser beam when the center of the laser beam presence detector 30 and the center of the beam exit 28 lie generally on the beam path 50 (e.g., within a tolerance of 0.01%, 0.05%, 0.1%, 1%, 2%, 5%, 10%, 20%, etc., of a diameter of the beam exit 28, or another suitable cross-sectional dimension thereof, if the beam exit 28 is not circular).

In such embodiments, a laser beam directed along the beam path 50 may not be sensed by the optical sensor 32 and, correspondingly, the sensor 32 may transmit a signal to the computer 66 indicating the absence of detection of the laser beam. If the laser beam path 50 is blocked by an edge of the beam exit 28, the scattered laser radiation may be sensed by the optical sensor 32. The interior surface of the beam exit 28 may be coated or polished to increase the reflectance thereof. Alternatively, if a portion of the sensor 32 near the inner perimeter of the beam exit 28 or the inner perimeter of the handpiece 20 lies directly on the beam path 50, the sensor 32 may sense a laser beam impinging directly thereupon. The sensor 32 may transmit a corresponding signal to the computer 66.

Figure 5A:
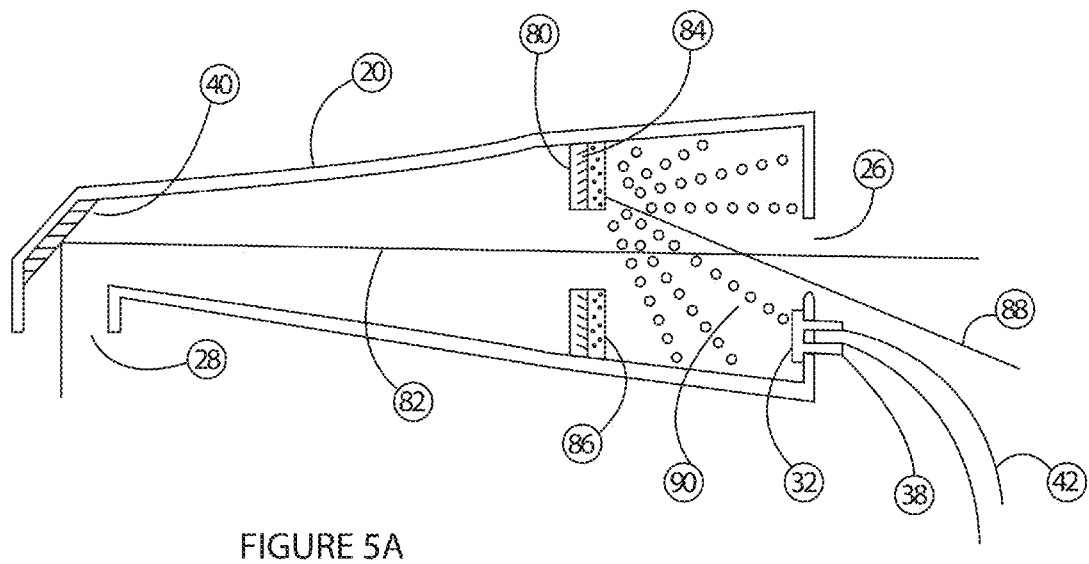
FIG. 5A is a cross-sectional view of a dental handpiece/main chamber assembly including a reflector ring and a detector, according to various embodiments.
Figure 5B:
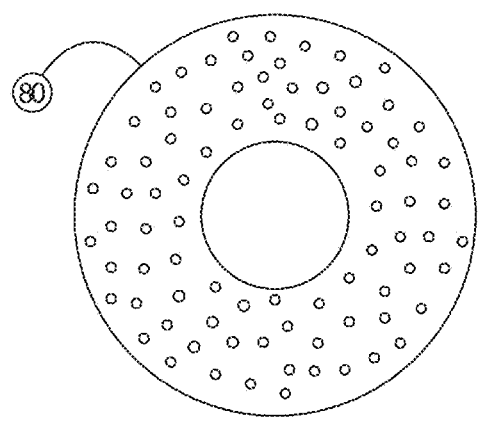
FIG. 5B schematically depicts a reflector ring mountable in a dental handpiece/main chamber assembly, according to various embodiments.

With reference to FIGS. 5A and 5B, in some embodiments a reflective ring 80 is disposed within the handpiece 20. The ring may be concentric with an optical axis 82 that exits the handpiece at a center of the beam exit 28. The ring 80 is configured to reflect laser radiation from a reflective surface 84 and to scatter laser radiation from a scattering surface 86. A laser beam 88 that is incident upon the ring may be reflected and scattered as diffuse light 90. The diffuse light 90 can be detected by a sensor/beam presence detector 32 facing the ring. If a laser beam is directed through an opening or aperture of the ring reflector 80, the laser beam passes through the aperture toward the turning mirror 40, propogates through the beam exit 28, and is directed towards a treatment area. The laser energy is not be reflected and/or scattered by the ring 80 and the sensor 30 may not detect any laser radiation or does not detect laser radiation above a specified threshold level.

The ring/sensor assembly can thus provide a feedback signal to a computer in response to the laser beam being directed at the ring or the opening therein. The size (e.g., a diameter for circular or oval apertures, a diagonal for other shapes such as square, rectangle, triangle, etc.) and shape of the opening can be selected such that a beam passing therethrough is aligned with the center of the beam exit within a specified tolerance. The tolerance can be specified in terms of a distance from the center such as, e.g., 0.01 µm, 0.5 µm, 1 µm, 2 µm, 10 µm, etc., or more. The tolerance can also be specified in terms of a percentage of the radius/diameter or another cross-sectional dimension of the beam exit 28, e.g., 0.1%, 0.5%, 1%, 4%, 10%, 15%, 20%, etc., within a particular cross-sectional dimension of the beam exit 28. In some embodiments, the tolerance can be specified as an angle relative to a normal to a cross-sectional surface of the beam exit such as, e.g., 0.01°, 0.1°, 0.5°, 1°, 1.5°, 5°, etc.

For use with such embodiments, the edge detection method described above may be modified as follows. The detection of a laser beam/radiation by the sensor 32 may indicate that the laser beam is not incident upon the center of the beam exit 28. The beam/radiation sensed by the sensor 32 may be incident upon a region of the ring 80 outside of a hollow central core. The detection of a laser beam/radiation by the sensor 32 may indicate that the laser beam is incident upon the a region of the ring 80 outside of the central core and/or on an inner surface of the beam exit 28 and/or the handpiece 20. The transition of the sensor output signal from detection of the laser beam/radiation to non-detection and/or from non-detection of the laser beam/radiation to the detection thereof, or both types of transitions, can be used to determine three or more co-ordinates of the non-core portion of the ring 80 and/or the co-ordinates of the inner surface of the beam exit 28 or the handpiece 20. These co-ordinates can then be used to determine the center of the ring 80 and, in effect, the center of the beam exit 28 that corresponds with the center of the ring 80.

The central core may be a region around the center of the ring 80 within a distance of 0.01%, 0.05%, 0.1%, 1%, 2%, 5%, 10%, 20%, etc., of a diameter of the beam exit 28, a diameter of the ring 80, or another suitable cross-sectional dimension of the beam exit 28 and/or the ring 80, if the beam exit 28 and/or the ring 80 are not circular. Such an embodiment may be used during operation of the laser, to check alignment in near-real time. Misalignment caused by movement of the articulated arm 14 can be continuously corrected, thus providing a more tightly controlled beam path and allowing a narrower handpiece/main chamber assembly 20 with a smaller beam exit 28, for improved ergonomics and easier manipulation of the handpiece/main chamber assembly 20 within a patient's mouth. The detachable sensor described with reference to FIG. 3 can be used instead of or in addition to a sensor disposed within the beam exit 28 and/or the handpiece 20.

Figure 6A:
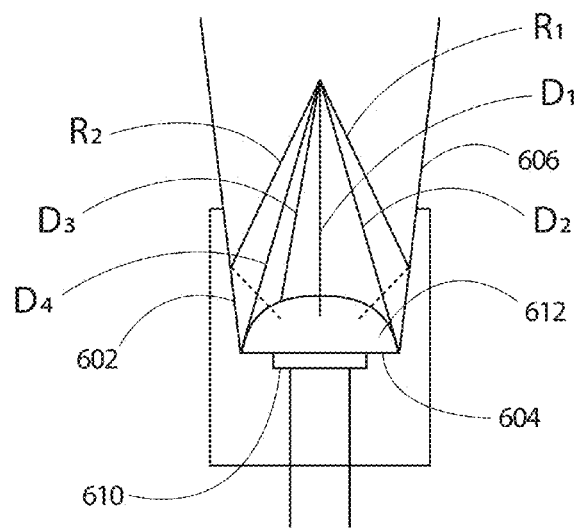
FIGS. 6A and 6B depict a detachable sensor and a corresponding plot showing an example relationship between an angle of the beam path and voltage detected by the sensor, according to various embodiments.
Figure 6B:
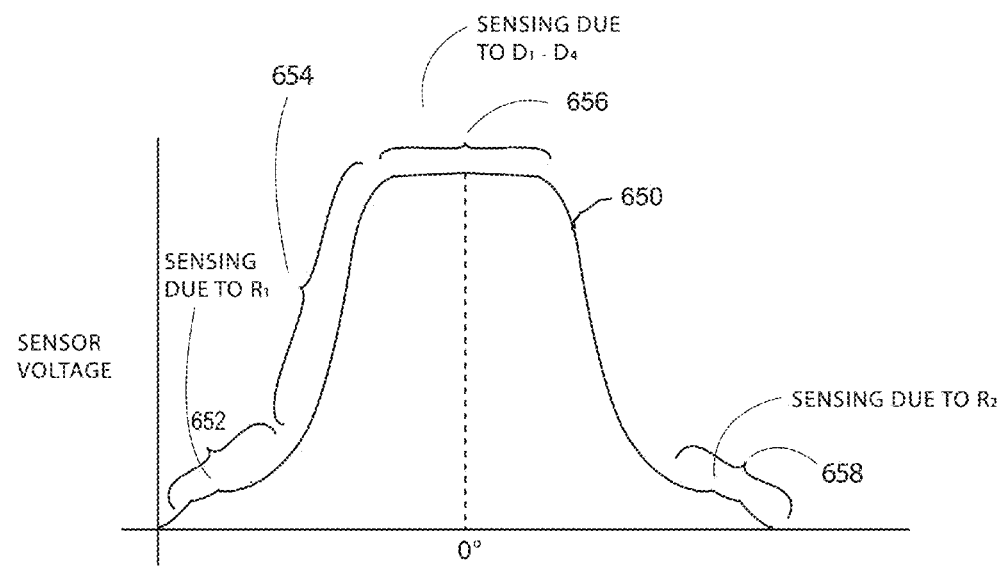

With reference to FIG. 6A, in an embodiment of a detachable sensor, laser beams may be directed to an outlet 604 of a beam exit 602 of a handpiece 20 and to an inner surface 606 of the beam exit 28 while performing edge detection, as described above. FIG. 6B shows the exemplary corresponding measurements by a sensor 610 optionally covered by a diffusor 612. In particular, beam R1 is directed to the inner surface 606 of the beam exit. Beam R1 may be absorbed by the inner surface and, as such, the sensor 610 may not detect any laser energy at all. In some cases, the beam R1 is at least partially reflected and/or scattered by the inner surface 606. As such, at least a portion of the laser energy of the beam R1 may be directed towards the diffusor 612 and/or the sensor 610, and may be detected thereby. In some embodiments, the sensor output is a voltage signal, and the portion 652 of the voltage signal 650 indicates the energy detected by the sensor 610 corresponding to the at least partially reflected and/or scattered beam R1. In FIG. 6B, the X axis corresponding to the voltage curve 650 is the beam angle relative to a normal to the outlet 604, where a beam along the normal (e.g., beam D1) passes through the center of the outlet 604.

In the example shown in FIG. 6A, beam D2 is directed to the edge of the outlet 604 of the beam exit 602, and beam D1 is directed approximately to the center of the beam exit. The sensor 610 can sense the energy corresponding to the beams D2 and D1 and other beams formed between these two beams. The sensor 610 can similarly sense the energy of beams D3 and D4, and of other beams formed between the beams D1 and D4. It should be understood that FIG. 6A depicts a cross-section of the beam exit 602 and the sensor 610. As such, several beams formed within a cone bounded by the beams D2 and D4 may be sensed by the sensor 610. As the energy of these beams is not attenuated by the beam exit 602, the output voltage of the sensor may increase rapidly, as indicated by the region 654. Beam R2 is directed towards the inner surface 606 of the beam exit 602. Like the beam R1, the energy of the beam R2 may not be detected at all by the sensor 610 or only a reflected and/or scattered portion of the energy of the beam R2 may be detected by the sensor 610. The portion 658 of the output voltage of the sensor 610 corresponds to such detected energy.

If a beam is moved from a beam path corresponding to the beam R1 to a beam path corresponding to the beam R2, and if this movement occurs along a diameter of the outlet 604 of the beam exit, the voltage curve 650 may be symmetrical and may have an approximately flat top 656, corresponding to the beams within the cone bounded by the beam paths D2 and D4. The center of the flat top 656 may correspond to the beam D1 passing through the center of the beam exit 602 within a specified tolerance. The rapid transition in the portion 654 (i.e., between portions 652 and 656), may be used for detecting edges of the outlet 604 of the beam exit 602. In general, it may be difficult to determine with sufficient accuracy whether the beam is moved along a diameter of the outlet 604 of the beam exit. As such, three or more edge points may be identified and the center of the beam exit may be determined by computing a centroid.

Figure 7A:
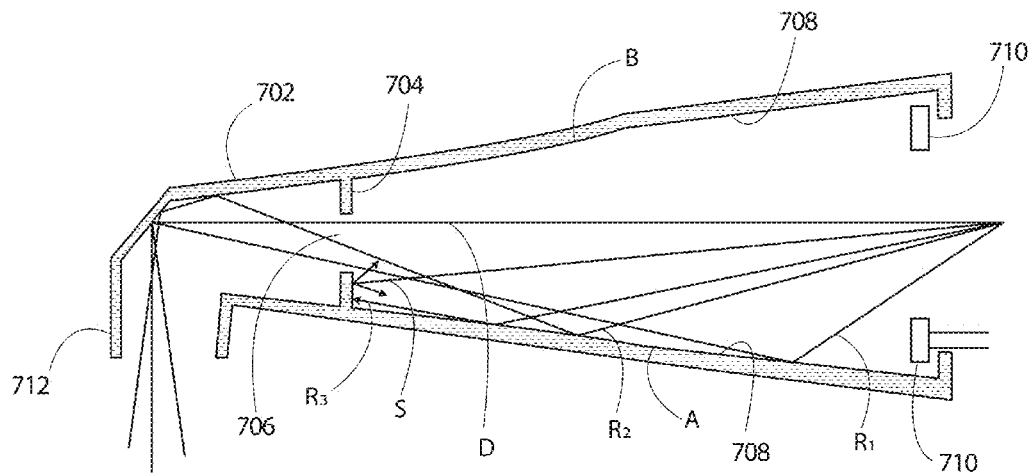
FIGS. 7A and 7B depict a reflector/sensor assembly mounted within a handpiece/main chamber assembly and a corresponding plot showing an example relationship between an angle of the beam path and voltage detected by the sensor, according to various embodiments.
Figure 7B:
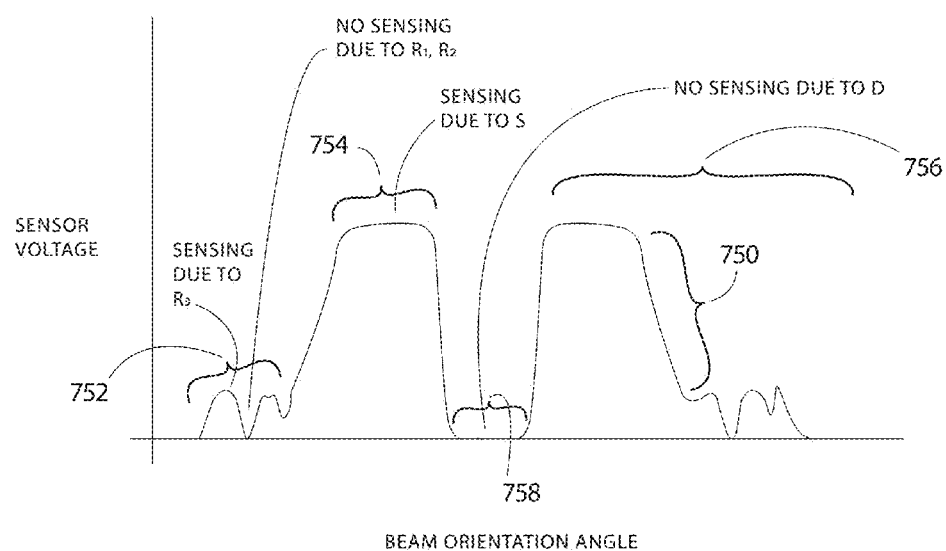

With reference to FIG. 7A, an exemplary handpiece 702 includes a sensor assembly. The sensor assembly includes a reflector ring 704 having a central aperture 706 and a sensor 710. Laser beams may be directed to the aperture 706, to the ring 704, and to the inner surface 708 of the handpiece 702 while determining the initial position of the beam guidance system. FIG. 7B shows the exemplary corresponding measurements by the sensor 710. In particular, beams R1 and R2 are directed to the inner surface 708, which may or may not reflect these beams. If reflected, in some cases the reflected beam may pass through the aperture 706 and would not be reflected by the ring 704. As such, energy from these beams may not be detected by the sensor 710. Beam R3 is also directed to the inner surface 708, but when reflected, the beam R3 is directed to the reflector ring 704. Therefore, at least a part of the laser energy of the beam R3 is reflected by the ring 704 towards the sensor 710. In response, the sensor 710 may generate an output signal. Typically, only a small portion, e.g., less than 50%, 20%, 5%, etc., of the energy of the beam R3 may be reflected by the inner surface 708 and only a fraction of that reflected energy may be reflected further by the ring 704. As such, the sensor output signal is a relatively weak signal.

In general, some of the laser beams along paths from the path of the beam R1 up to a path of a beam directed to a joint between the inner surface 708 and the reflector ring 704 may be reflected by the inner surface 708 and may pass through the aperture 706. Some of these beams may be reflected by the ring 704, and at least a part of the energy thereof may be sensed by the sensor 710. A typical voltage signal corresponding to such signals is indicated by the portion 752 of the voltage signal 750. In FIG. 7B, the X axis corresponding to the voltage curve 750 is the beam angle relative to a normal to the aperture 706, where a beam along the normal (e.g., beam D) passes through the center of the beam exit 712.

If a laser beam, such as the beam S, is directly incident upon the reflector ring 704, a significant portion (e.g., more than 30%, 40%, 50%, 75%, etc.) of the energy of the beam may be reflected by the ring 704. The ring 704 may include a diffusor. The sensor 710 may sense the reflected and optionally diffused laser energy and, in response, may produce an output signal corresponding to the portion 754 of the voltage signal 750. As the beams similar to the beam S are not incident upon the inner surface 708 of the handpiece 702, these rays are not attenuated by the handpiece 20 before they are reflected by the ring 704. As such, the energy sensed by the sensor 710 is typically much greater (e.g., 2, 3, 10, 100, etc. times) the energy sensed corresponding to the reflection of beams such as the beam R3. Therefore, the portion 754 of the sensor output signal 750 is typically much stronger (e.g., 2, 5, 10, 20, 50, 100, 400, etc. times) than the maximum strength of the sensor output signal within the region 752.

The laser beams such as the beam D, that have sufficiently small angles relative to the normal to the aperture 706, may pass through the aperture 706. As such, these beams are not reflected by the reflector ring 704 nor are they reflected by the inner surface 708 and little or no energy of these beams may be sensed by the sensor 710. As such, as indicated at the portion 758, the sensor output may drop significantly, e.g., less than 5%, 1%, 0.1%, etc., of the sensor output corresponding to the portion 754 of the sensor output signal 750.

If a beam is moved from a beam path corresponding to the beam R1 on side A of the handpiece 702 to a similar beam path on side B of the handpiece, and if this movement occurs along a diameter of the aperture 706, the voltage curve 750 may be symmetrical as indicated by the portion 756, and may have an approximately flat trough 758 corresponding to the beams directly passing through the aperture 706. The center of the portion 758 may correspond to the beam D passing through the center of the aperture 706 and the beam exit 712 within a specified tolerance. The rapid transition between the portions 752, 754 may be used to first determine the aperture edge and then used to determine whether the beam is directed to the inner surface 708 or to the reflector ring 704. The rapid transition between the portions 758, 756 may be used to determine the center of the beam exit 712. In general, it may be difficult to determine with sufficient accuracy whether the beam is moved along a diameter of the aperture 706 of the reflector 704. As such, three or more points identifying the aperture boundary may be identified and the center of the beam exit may be determined by computing a centroid.

Figure 8:
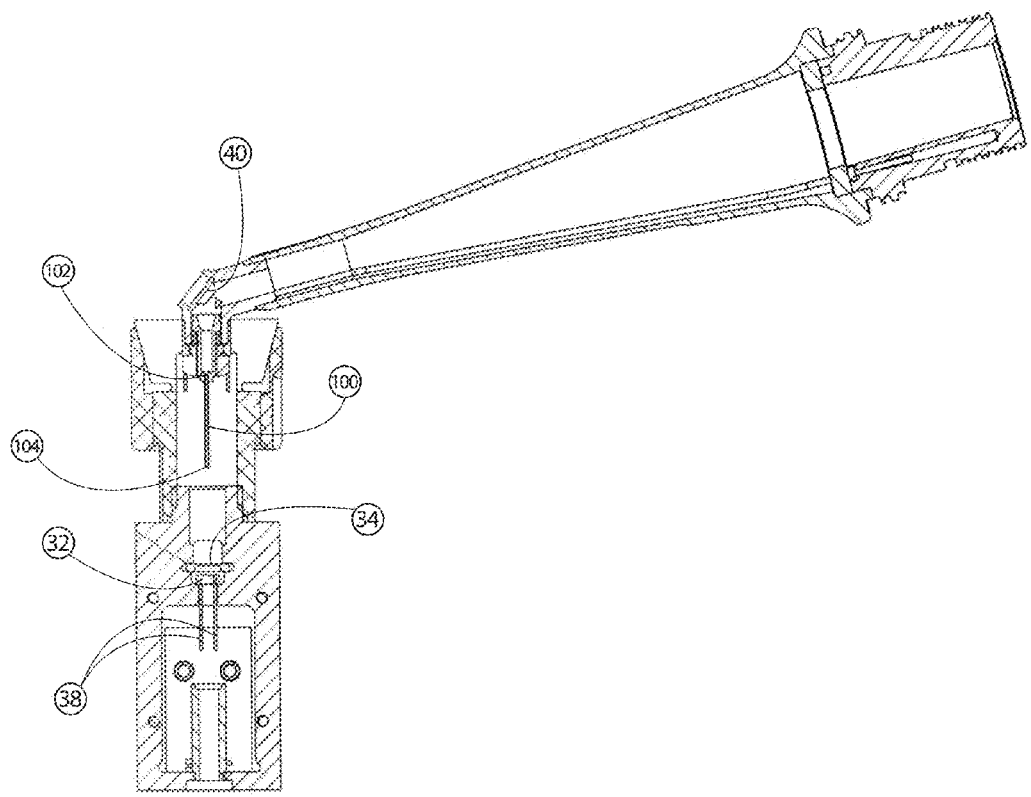
FIG. 8 is a cross-sectional view of a dental handpiece/main chamber assembly including a hollow waveguide and a detachable laser beam presence detector, according to various embodiments.

Certain dental soft tissue procedures or periodontal procedures may be performed using a hollow waveguide. With reference to FIG. 8, a laser beam having a wavelength in the far infrared region, e.g., in a range of 9-11 micrometers, may be coupled into a hollow waveguide 100. To this end, in some embodiments, the laser beam is focused to a waist, w, such that the waist is formed at an inlet 102 of the hollow waveguide 100. In various embodiments, waveguide throughput efficiency can be increased or maximized if the beam waist to waveguide bore radius ratio, w/a, is approximately 0.64. Some hollow waveguides that are well suited for dental soft tissue, or periodontal treatment have inner diameters (bore diameters) in a range of 0.3-2.0 mm, 0.4-1.0 mm, or 0.6-0.8 mm. The corresponding beam waist diameters that can be well coupled into these hollow waveguides are about 0.19-1.26 mm, 0.26-0.64 mm, and 0.38-0.50 mm, respectively.

In various embodiments, such waist diameters can be achieved by focusing the laser beam slowly, i.e., by using relatively long focal lengths in the range of about 25 mm-200 mm, e.g., about 135 mm. Due to these long focal lengths (i.e., 25 mm or longer) the tolerance for angular misalignment of the laser beam is low. A relatively small angular misalignment can cause a significant displacement of the waist along a surface that is normal to the beam path, such that the laser beam is not coupled at all or is at least not adequately coupled with the waveguide inlet 102. In general, the displacement D of the laser beam waist at focus may be approximated as $D=f*\delta$, where f is focal length and $\delta$ is angular error. For example, an angular error of 0.5 mrad and a focal length of 150 mm yield a displacement of approximately 0.08 mm at focus.

In some embodiments, an automatic beam-alignment system can be used for coupling a laser beam into a hollow waveguide. In FIG. 8, for example, a handpiece having a hollow waveguide 100 of about 0.60 mm diameter is shown with an automatic alignment system. A sensor 32 is located after an outlet 104 of the hollow waveguide 100. A diffuser 34 may be placed over the sensor 32. The use of the diffusor is optional. In some embodiments, a pilot laser that is collinear with the infrared treatment laser is selected and is directed toward the waveguide 100. The sensor 32 can sense the presence and intensity of the pilot laser at the outlet 104 of the waveguide 100.

Therefore, in some embodiments, a beam guidance system may scan the pilot laser in a cross-sectional region over the inlet 102 of the hollow waveguide 100 in steps, as directed by a computer. At each step, the sensor 32 can measure the intensity of the pilot light emitted from the outlet 104. Using a centroid determination algorithm, the location of the center of the hollow waveguide inlet 102 can be determined by determining three or more points on the edge of the inlet 102. An initial position of the beam guidance system such that the beam is directed to the center of the inlet 102 of the waveguide 100 can then be determined, as described above. Both the pilot and the infrared laser beam may then be directed, via the beam guidance system, to the center of the hollow waveguide inlet, so as to improve or maximize coupling of the laser beam(s) to the waveguide.

In some embodiments, such as one or more of those described with reference to FIGS. 3-8, a photoresistor is used as the optical sensor 32. The photoresistor is typically sensitive to light having a wavelength of 532 nm which, for example, may be the wavelength of the marking/aiming laser beam. A translucent foam may be used as the optical integration element 34 and may be used to cover the photoresistor so that any laser light passing through the beam exit 28 is scattered and may be distributed substantially evenly on the optical sensor 32. The photoresistor may be configured to form a portion of a voltage divider and the voltage divider output may be fed into a comparator, which can measure the voltage divider output against a reference voltage. The comparator circuitry can be implemented in different ways with options including, but not limited to, having (i) an integrated circuit comparator (ii) an analog comparator using an operational amplifier, (iii) a digital comparator using an A/D converter, and/or (iv) a hardware or software controlled setpoint. The comparator output may be either high or low, depending on whether the photoresistor is sensing light (laser beam/radiation) or not. The comparator can be connected to a microprocessor which may serve as the computer 66, and which communicates with the galvanometer controller 60 via a serial connection which may serve as the computer control signal path 70.

Figure 9:
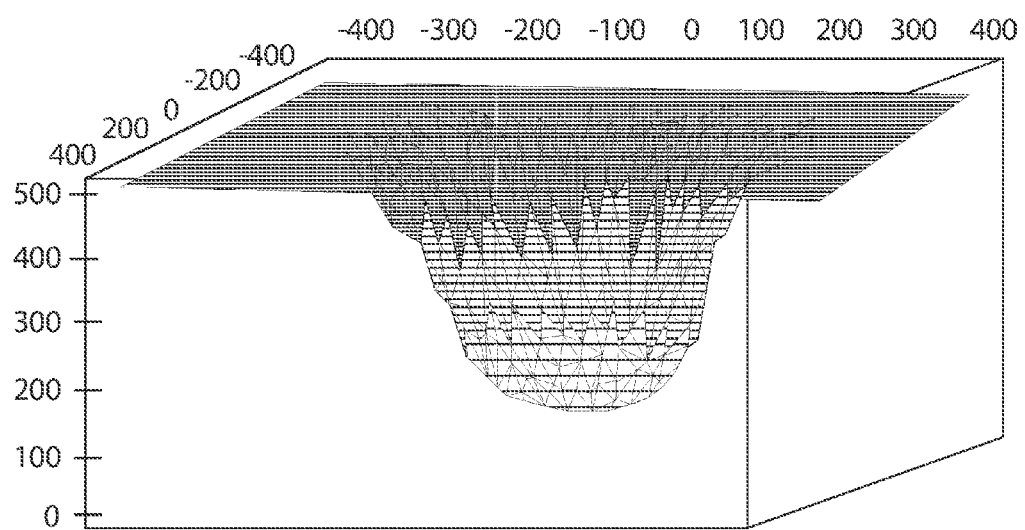
FIG. 9 is a plot showing an example relationship between the co-ordinates of a beam guidance system and voltage measured by a sensor, according to various embodiments.

FIG. 9 graphically depicts additional sensor measurements, such as those shown in FIGS. 6B and 7B. In FIG. 9, the X and Y axes indicate the X and Y coordinates, respectively, of the position of a beam guidance system having X and Y galvo-controlled mirrors. The Z axis indicates the sensor output voltage. In the embodiment used to obtain these measurements, the sensor outputs a low voltage, e.g., between 200-300 mV when it detects laser energy and a high voltage, e.g., 400-500 mV, when the sensor detects little or no laser energy. A sensor using one or more photoresistors can provide such voltage signals. It is seen from FIG. 9 that if a nominal home position of the X and Y galvo-controlled mirrors is set to (−130, 0), the laser beam may be directed through a center of a beam exit.

Figure 10A:
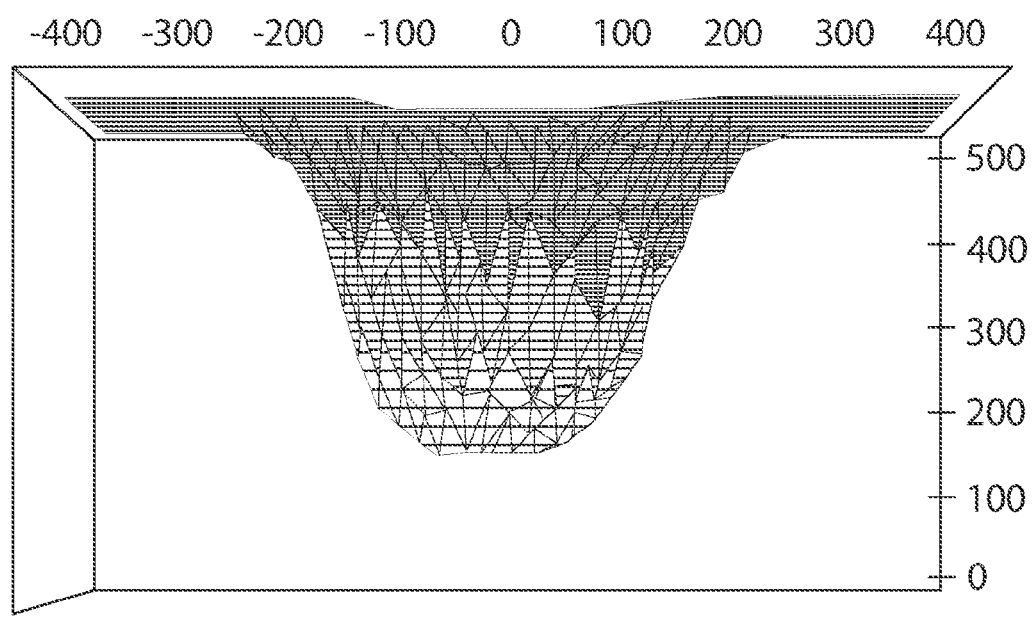
FIG. 10A is a plot showing an example relationship between the co-ordinates of a beam guidance system and voltage measured by a sensor located downstream from a hollow waveguide, according to various embodiments.
Figure 10B:
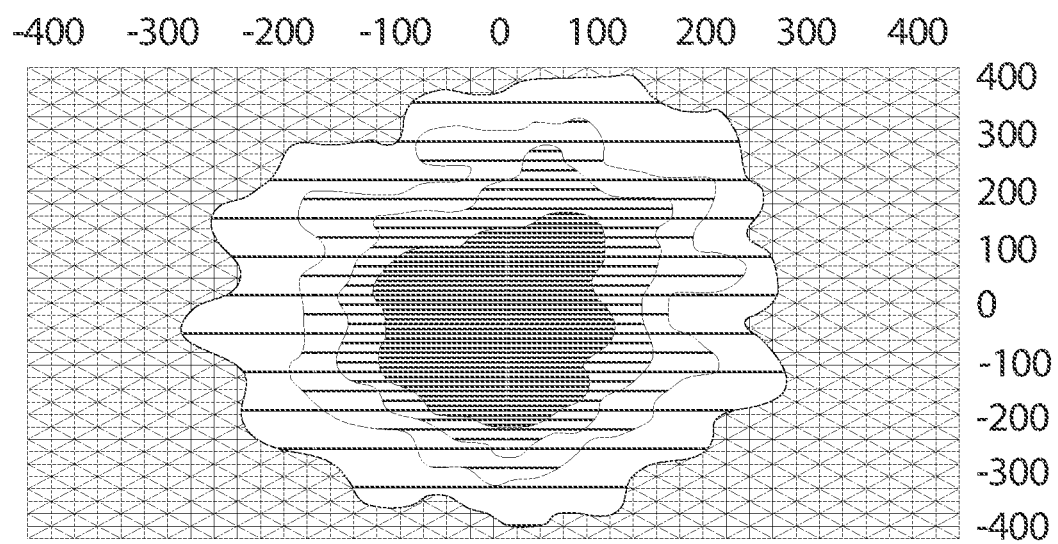
FIG. 10B is a plan view of the plot shown in FIG. 10A.

FIGS. 10A and 10B show exemplary sensor measurements obtained when the laser beam is coupled to a hollow waveguide as described above with reference to FIG. 8. It is seen in FIG. 10A that when the beam waist is aligned with the waveguide inlet within a specified tolerance, the sensor voltage is low, e.g., in the range 150-225 mV. When the beam waist is misaligned, the sensor output voltage is high, e.g., between 400-600 mV. The plot shown in FIG. 10B can be obtained by transforming the three-dimensional plot shown in FIG. 10A into a two-dimensional plot, where different ranges of sensor output voltages can be assigned different colors, shades, patterns, etc. FIGS. 10A and 10B show that if a nominal home position of the X and Y galvo-controlled mirrors is set to (−25, 0), the laser beam may be well coupled to the hollow waveguide.

FIGS. 9, 10A, and 10B illustrate that the low and high sensor output voltage values may not be associated with absolute ranges and, instead, may be relative to each other. It should be understood that voltage is only one kind of sensor output and that different sensors may represent the sensed energy via other indicators such as current, resistance, capacitance, temperature, etc. In some cases a high sensor output signal may be produced corresponding to the detection of laser energy above a specified threshold. In other cases, however, a low sensor output signal may be produced corresponding to the detection of laser energy above that threshold. An initially obtained sensor output signal may be transformed into a suitable electrical signal used in further analysis thereof using additional circuitry.

Figure 11A:
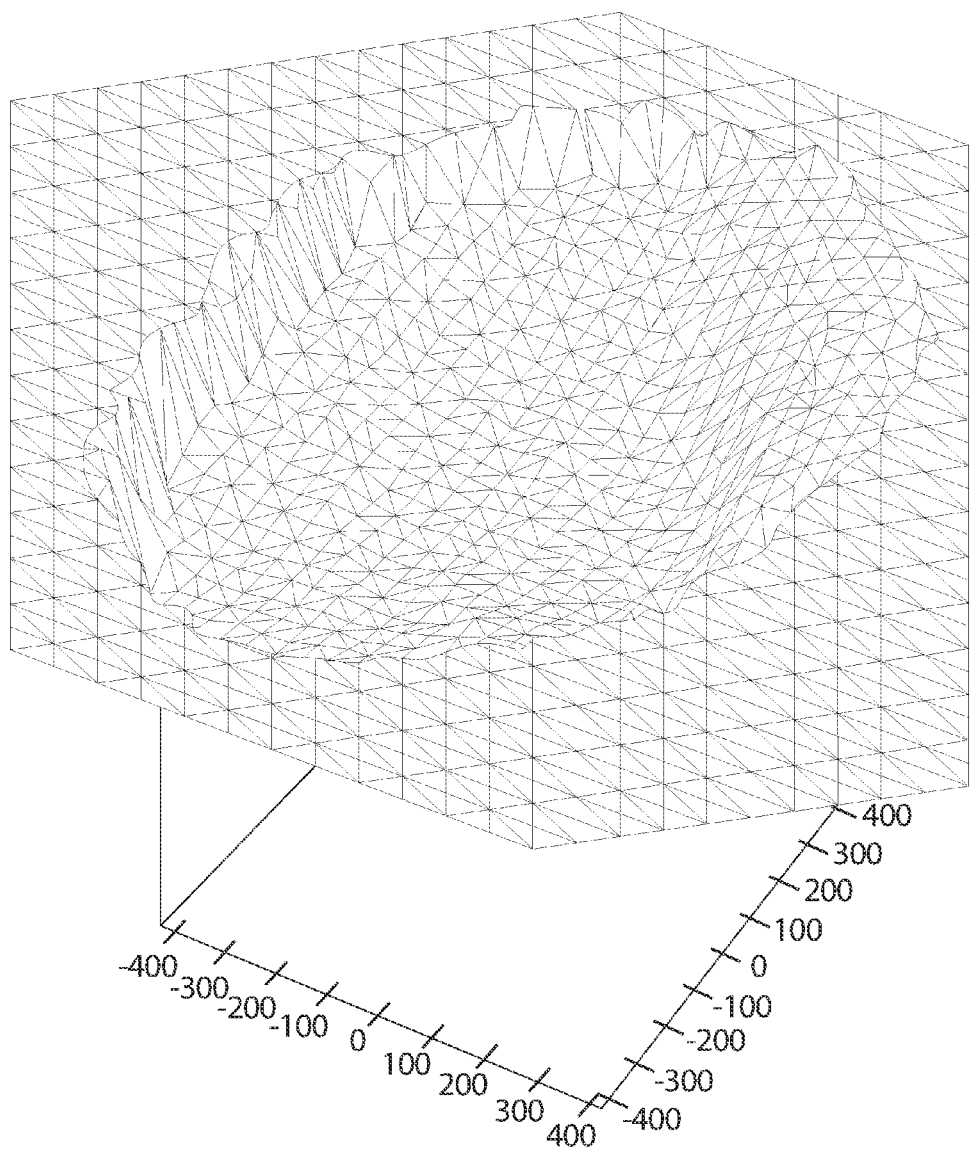
FIG. 11A is an isometric view of a sensor signal corresponding to an embodiment having a handpiece without a hollow waveguide.
Figure 11B:
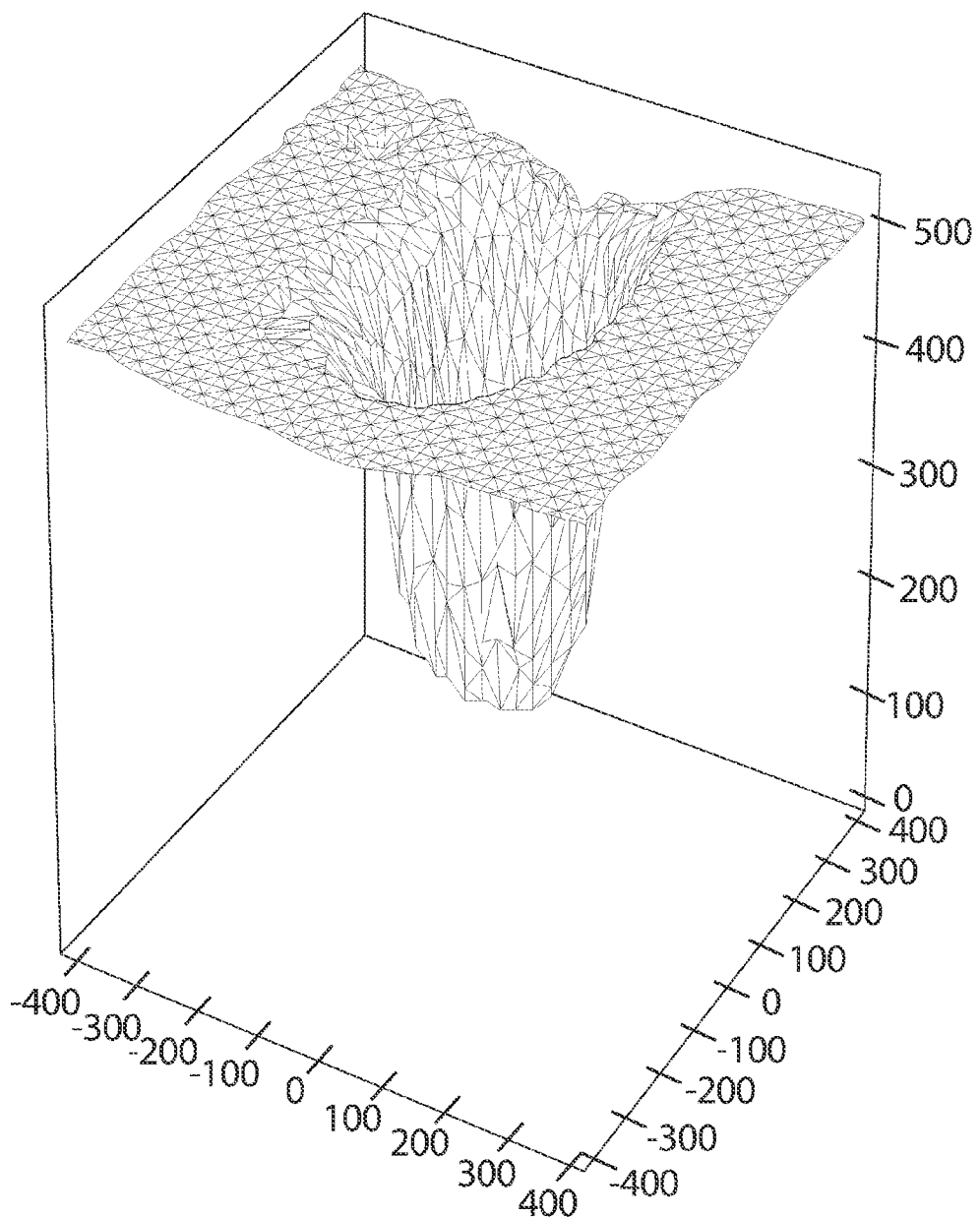
FIG. 11B is an isometric view of a sensor signal corresponding to another embodiment having a handpiece that includes a hollow waveguide.
Figure 12A:
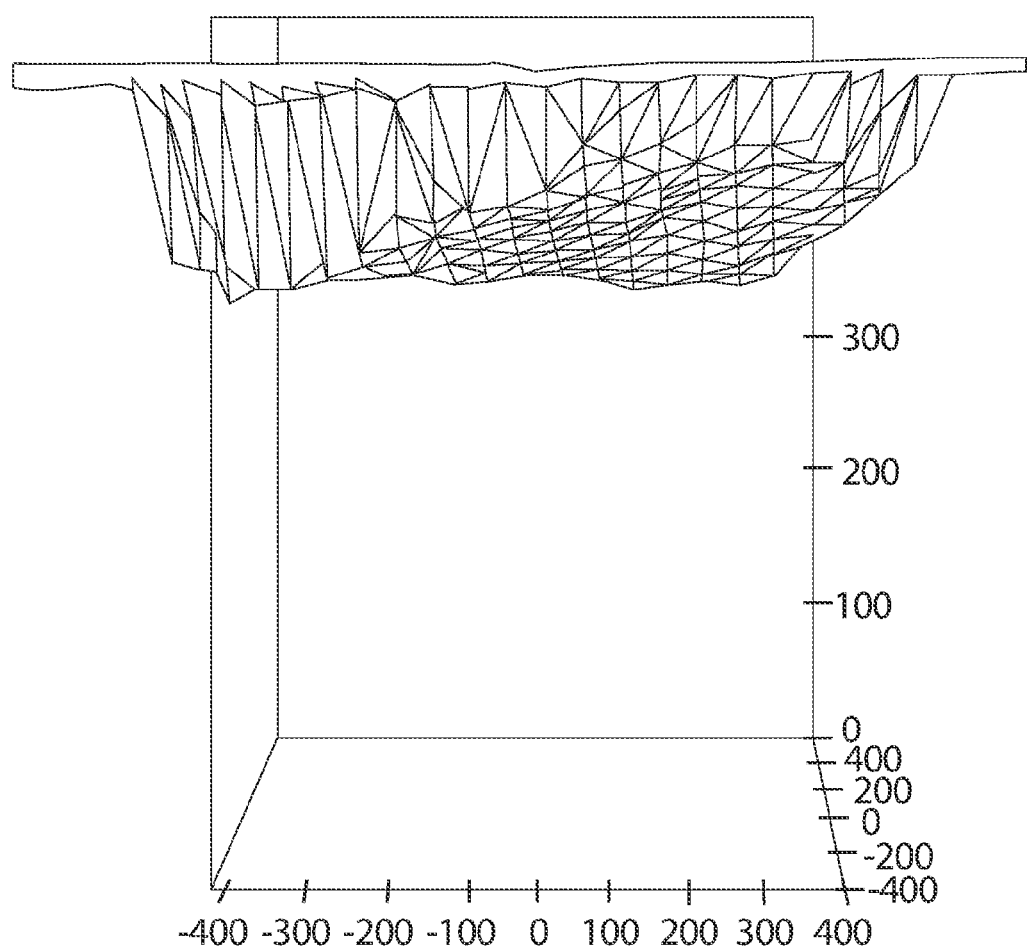
FIG. 12A is a side view of the sensor signal corresponding to FIG. 11A.
Figure 12B:
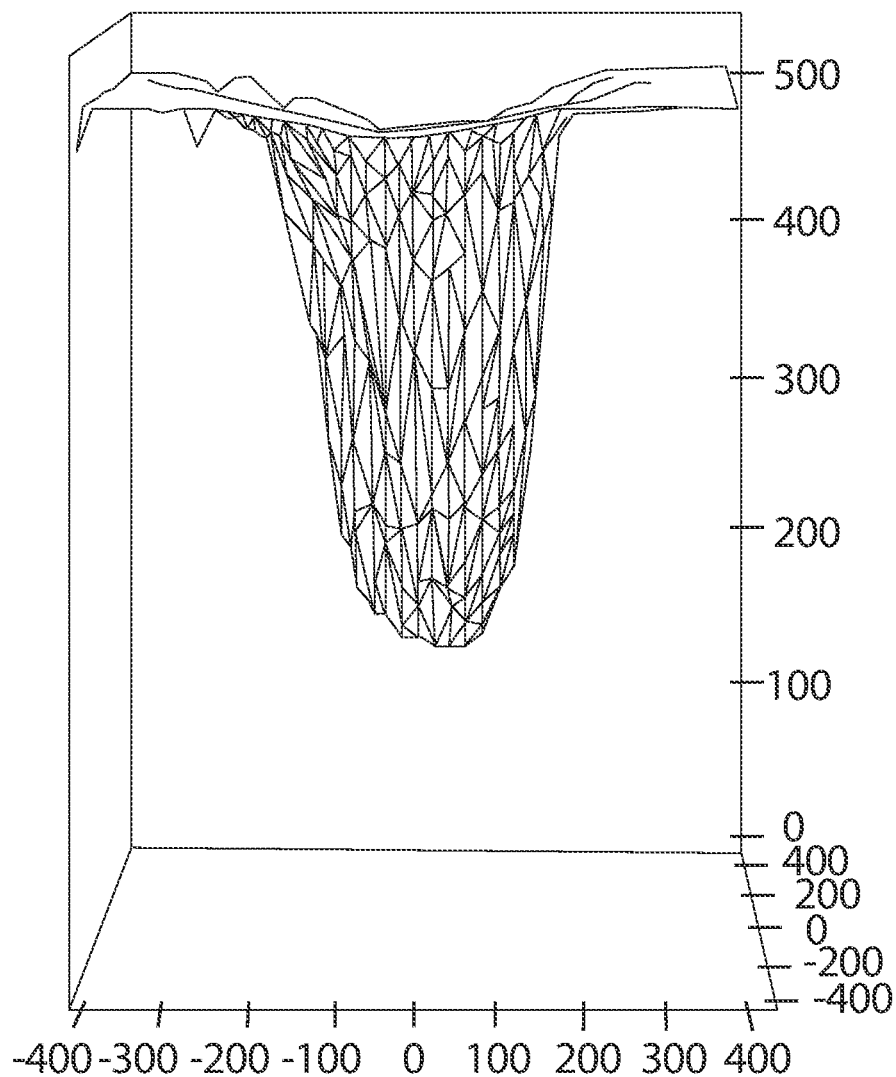
FIG. 12B is a side view of the sensor signal corresponding to FIG. 11B.

FIG. 11A is an isometric view of an exemplary sensor-measurement graph obtained using a handpiece having a beam exit, such as that depicted in FIG. 3. FIG. 11B is an isometric view of an exemplary sensor-measurement graph obtained using a handpiece having a hollow waveguide, such as that depicted in FIG. 8. The inner diameter of the waveguide is approximately 600 µm. The sensor was located downstream from the waveguide outlet. FIG. 12A shows a side view of the sensor-measurement graph shown in FIG. 11A, and FIG. 12B shows a side view of the sensor-measurement graph shown in FIG. 11B. In FIGS. 11A through 12B, the X and Y axes indicate the X and Y coordinates in galvanometer-step units, respectively, of the position of a beam guidance system having X and Y galvanometer mirrors 64. The Z axis indicates the sensor output voltage.

The sensor response shown in FIGS. 11A and 12A is relatively flat compared to the sensor response shown in FIGS. 11B and 12B. This shows that across a wide range of movement of the X and Y galvo-controlled mirrors the laser beam may pass through the beam exit 28 of the handpiece 20 and can be detected by the sensor 32. Specifically, FIG. 12A shows that the X coordinate of the beam guidance system can vary from approximately −400 up to approximately +300 galvanometer-step units. On the other hand, when the handpiece includes a hollow waveguide, the X and Y galvanometer mirrors 64 can be moved within a relatively narrow range, such that the laser beam is effectively coupled with the waveguide and laser energy at the waveguide outlet can be detected by the sensor 32. For example, FIG. 12B shows that the X coordinate of the beam guidance system can vary from about −100 up to about +100 galvanometer-step units.

In some embodiments using a comparator as described above, a comparator threshold can be determined by computing a noise floor, where the noise floor represents the typical sensor output when the sensor 32 detects reflected laser energy such as that described with reference to FIGS. 6A through 7B. The noise floor can be seen in FIG. 10A at a voltage of about 500 mV. A signal above this threshold (in embodiments in which a lower voltage is output by the sensor 32 upon detecting greater laser energy) can be designated as a signal indicating absence of laser energy or absence of laser energy above a specified energy-level threshold. In some embodiments, the sensor is used to determine the type of the handpiece 20 used. To this end, the galvanometer mirrors 64 can be adjusted such that the sensor 32 detects a laser beam. Then, one or both mirrors 64 are moved at a step size that corresponds to the size of a beam exit 28 of a handpiece 20 that does not include a hollow waveguide 100. If the handpiece 20 being used is of this type, i.e., it does not include a waveguide 100, the sensor 32 may still detect the laser beam. On the other hand, if the handpiece 20 being used includes a waveguide 100, the sensor 32 may not detect laser energy above a specified energy threshold. The sensor signal may change, indicating the use of a handpiece 20 having a hollow waveguide 100. Beam exit edge detection or waveguide inlet edge detection may then be performed as described herein. One form of software code useful in this analysis is shown in Appendix A.

Referring back to FIG. 3, with the laser beam actuated, the galvanometers 22 may be moved in a spiral or a random pattern from their nominal home positions by the computer 66 and galvanometer controller 60 in discrete steps or continuously. If the laser beam passes through the beam exit 28, it would typically cause the resistance of the photoresistor to drop significantly, causing the comparator output/state to go from high to low, in some embodiments. After each step, the galvanometer controller 60 can read the comparator state from the microprocessor. When the state is low, the spiral pattern may be stopped and the microprocessor can begin an edge detection procedure.

During the edge-detection procedure, the galvanometer controller 60, as directed by the computer 66, may move the mirrors one at a time, to locate the edge coordinates along one axis and then along one or more other axes. In one embodiment, the edge detection procedure uses a binary search with an initial maximum step of the beam exit 28 radius $r_A$. A different initial maximum step that is a function of the beam exit radius $r_A$, or is independent thereof, may be used in other embodiments. Initially, the galvanometer mirror 64 is moved such that the comparator value is low, indicating that the laser beam is passing through the beam exit 28. An axis is selected for edge detection, and a single galvanometer mirror 64 is moved in one direction along the selected axis in steps of $r_A$ until the comparator value goes back to its high value, indicating that the laser beam is no longer passing through the beam exit 28. According to the procedure, that galvanometer mirror 64 is then moved in the opposite direction along the selected axis in steps of $r_A/2$ until the comparator reports a low value. The search direction is then changed again, and the galvanometer mirror 64 is moved in the opposite direction along the selected axis, in steps of $r_A/4$ until the comparator changes state again. This search process is repeated until the edge location along the selected axis is determined according to a selected precision, for example $r_A/8$, $r_A/16$, $r_A/20$, $r_A/25$, $r_A/50$, $r_A/100$, etc.

Once the first edge is located according to a selected precision and along the selected axis, the same galvanometer mirror 64 may be moved in the direction opposite its first initial movement. Then, the same procedure described above, which may include repeated movements of the galvanometer in alternating directions along the selected axis, can be used to find the second edge point along the selected axis. Once the two edge coordinates along a single axis are determined, their values are averaged and that galvanometer mirror 64 is set to the coordinate corresponding to the computed average, which may represent the center coordinate of the beam exit 28 along the selected axis. The edge detection process may then be repeated using the second galvanometer mirror 64 along an axis that is orthogonal to the selected axis. The coordinate of the other galvanometer mirror 64 may be set to the average of the two edge points determined along the orthogonal axis. These two coordinates may then be stored in a memory associated with the computer 66 (e.g., a microprocessor) and/or the galvanometer controller 60, as the center of the beam exit 28.

In some embodiments, the beam guidance system of the dental laser system 10 is located within the handpiece/main chamber assembly 20. A beam splitter may be included after the beam guidance system along the beam path. The beam splitter may be configured to direct a portion of the laser beam to a beam presence detector not located within the handpiece/main chamber assembly or near the beam exit 28, as described above. The location of the beam presence detector may be calibrated with the handpiece/main chamber assembly and the beam splitter in order to provide alignment of the handpiece/main chamber assembly and beam path based upon the feedback of the beam path that is split and directed to the beam presence detector. The beam presence detector and the computer 66 may communicate with each other using wireless transmitters/receivers.

Having described herein illustrative embodiments, persons of ordinary skill in the art will appreciate various other features and advantages of the invention apart from those specifically described above. It should therefore be understood that the foregoing is only illustrative of the principles of the invention, and that various modifications and additions can be made by those skilled in the art without departing from the spirit and scope of the invention. Accordingly, the appended claims shall not be limited by the particular features that have been shown and described, but shall be construed also to cover any obvious modifications and equivalents thereof.

What is claimed is:

1. A beam-alignment system for aligning a laser beam of a laser-based treatment apparatus, the system comprising:
   a housing forming an inlet to a beam exit of a handpiece of a laser-based treatment apparatus; and
   a sensor disposed in the housing, aligned with the inlet and adapted to provide a first signal indicating detection of laser energy by the sensor above a specified threshold level and a second signal indicating absence of laser energy above the threshold level; and
   a processor programmed to:
     direct a beam guidance system to adjust a laser beam path; and
     determine a center of the beam exit using the first and second signals.

2. The beam-alignment system of claim 1, wherein the housing is attachable to the beam exit via at least one of a friction-based coupling, a threaded coupling, a magnetic coupling, and a mechanical coupling.

3. The beam-alignment system of claim 1, wherein the sensor comprises at least one sensor element selected from the group consisting of a photoresistor, a photodiode, a phototransistor, a thermoelectric device, and a far-IR optical sensor.

4. The beam-alignment system of claim 1, wherein the sensor is adapted to provide the second signal indicating absence of laser energy.

5. The beam-alignment system of claim 1, further comprising a diffusor disposed over the sensor.

6. The beam-alignment system of claim 5, wherein the diffusor comprises a translucent material.

7. The beam-alignment system of claim 1, further comprising an amplifier for amplifying an output signal of the sensor.

8. The beam-alignment system of claim 1, further comprising circuitry:
comparing a sensor signal obtained from the sensor with a reference signal corresponding to the threshold level;
producing the first signal if the sensor signal is greater than the reference signal; and otherwise producing the second signal.

9. A laser-based treatment system, comprising:
a handpiece comprising:
a beam exit; and
a sensor assembly: (i) that has a central aperture aligned with the beam exit, and (ii) that is at least partially attached to an inner surface of the handpiece, the sensor assembly being adapted to provide a first signal indicating detection of laser energy by the sensor assembly above a specified threshold level and a second signal indicating absence of laser energy above the specified threshold level; and
a processor programmed to:
direct a beam guidance system to adjust a laser beam path; and
determine a center of the beam exit using the first and second signals.

10. The laser-based treatment system of claim 9, wherein at least a portion of the inner surface of the handpiece is reflective at a wavelength of the laser.

11. The laser-based treatment system of claim 9, wherein the sensor assembly comprises at least one sensor selected from the group consisting of a photoresistor, a photodiode, a phototransistor, a thermoelectric device, and a far-IR optical sensor.

12. The laser-based treatment system of claim 9, wherein the handpiece further comprises a turning mirror.

13. The laser-based treatment system of claim 12, wherein:
the turning mirror is disposed downstream of the sensor along a first portion of a laser-beam path and upstream from the beam exit along a second portion of the laser-beam path; and
the beam exit and the aperture of the sensor assembly are aligned via the first and second portions.

14. The laser-based treatment system of claim 9, wherein a translucent material is disposed over the sensor assembly.

15. The laser-based treatment system of claim 9, further comprising an amplifier for amplifying an output signal of the sensor assembly.

16. The laser-based treatment system of claim 9, further comprising circuitry:
comparing a sensor signal obtained from the sensor assembly with a reference signal;
producing the first signal if the sensor signal is above the reference signal; and
otherwise producing the second signal.

17. The laser-based treatment system of claim 9, wherein the sensor assembly comprises:
an annular reflector attached to the inner surface of the handpiece and forming the central aperture; and
a sensor separated from and facing the reflector ring, and adapted to produce the first and second signals.

18. The laser-based treatment system of claim 17, wherein the annular reflector comprises a diffusor.

19. A method of aligning a laser beam, the method comprising the steps of:
(a) selecting a first axis and a step size;
(b) adjusting a first rotatable mirror of a beam guidance system such that a laser beam directed by the beam guidance system is not detected by a sensor and recording a co-ordinate of the first mirror along the first axis;
(c) adjusting the first rotatable mirror along the first axis in a first direction by the step size and recording a co-ordinate of the first mirror along the first axis;
(d) if the laser beam is not detected, increasing the step size and repeating step (c);
(e) otherwise:
(A) decreasing the step size and readjusting the first rotatable mirror along the first axis in a second direction opposite the first direction by the decreased step size;
(B) if the laser beam is detected, computing an average of the co-ordinates recorded in steps (b) and (c), the average being associated with the first rotatable mirror;
(C) otherwise, replacing the co-ordinate recorded in step (b) corresponding to the readjusted position of the first rotatable mirror along the first axis;
(D) decreasing the step size and readjusting the first rotatable mirror along the first axis in the first direction by the decreased step size;
(E) if the laser beam is not detected, computing an average of the co-ordinates recorded in steps (C) and (c), the average being associated with the first rotatable mirror; and
(F) otherwise, replacing the co-ordinate recorded in step (c) corresponding to the readjusted position of the first rotatable mirror along the first axis.

20. The method of claim 19, further comprising repeating steps (e)(A) through (e)(F).

21. The method of claim 19, further comprising:
selecting a second axis orthogonal to the first axis; and
repeating steps (b) through (e) corresponding to the second axis and a second rotatable mirror, the average computed in any of steps (e)(B) and (e)(E) being associated with the second rotatable mirror.

* * * * *